United States Patent
Larsen et al.

(10) Patent No.: US 12,421,536 B2
(45) Date of Patent: *Sep. 23, 2025

(54) METHODS OF PROCESSING LIGNOCELLULOSIC BIOMASS USING SINGLE-STAGE AUTOHYDROLYSIS AND ENZYMATIC HYDROLYSIS WITH C5 BYPASS AND POST-HYDROLYSIS

(71) Applicant: New Energy Blue LLC, Lancaster, PA (US)

(72) Inventors: Jan Larsen, Tommerup (DK); Niels Nielsen Poulsen, Vojens (DK); Martin Dan Jeppesen, Odense V (DK); Kit Kellebjerg Mogensen, Fredericia (DK)

(73) Assignee: New Energy Blue LLC, Lancaster, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/523,358

(22) Filed: Nov. 29, 2023

(65) Prior Publication Data

US 2024/0102064 A1 Mar. 28, 2024

Related U.S. Application Data

(63) Continuation of application No. 17/329,960, filed on May 25, 2021, now Pat. No. 11,866,753, which is a continuation of application No. 14/418,667, filed as application No. PCT/DK2013/050256 on Aug. 1, 2013, now Pat. No. 11,118,203.

(60) Provisional application No. 61/678,130, filed on Aug. 1, 2012.

(30) Foreign Application Priority Data

Aug. 1, 2012 (DK) .......................... PA 2012 70461

(51) Int. Cl.
| | |
|---|---|
| C12P 19/14 | (2006.01) |
| C12P 7/10 | (2006.01) |
| C12P 19/02 | (2006.01) |
| C13K 1/02 | (2006.01) |
| C13K 13/00 | (2006.01) |
| D21C 1/04 | (2006.01) |
| D21C 3/04 | (2006.01) |

(52) U.S. Cl.
CPC ................. *C12P 19/14* (2013.01); *C12P 7/10* (2013.01); *C12P 19/02* (2013.01); *C13K 1/02* (2013.01); *C13K 13/002* (2013.01); *D21C 1/04* (2013.01); *D21C 3/04* (2013.01); *C12P 2201/00* (2013.01); *Y02E 50/10* (2013.01)

(58) Field of Classification Search
CPC .. C12P 19/14; C12P 7/10; C12P 19/02; C12P 2201/00; C13K 1/02; C13K 13/002; D21C 1/04; D21C 3/04; Y02E 50/10
See application file for complete search history.

(56) References Cited

U.S. PATENT DOCUMENTS

| | | |
|---|---|---|
| 2008/0138862 A1 | 6/2008 | Felby et al. |
| 2009/0209009 A1 | 8/2009 | Tolen et al. |
| 2011/0147409 A1 | 6/2011 | Vibe-Pedersen et al. |
| 2011/0162741 A1 | 7/2011 | Fink et al. |
| 2012/0104313 A1 | 5/2012 | Garbergo |
| 2012/0115200 A1 | 5/2012 | Dottori et al. |
| 2015/0191758 A1 | 7/2015 | Larsen et al. |

FOREIGN PATENT DOCUMENTS

| | | |
|---|---|---|
| CN | 102171353 A | 8/2011 |
| CN | 102388144 A | 3/2012 |
| EP | 2 169 074 A1 | 3/2010 |
| WO | WO 2009/003292 A1 | 1/2009 |
| WO | WO 2010/134455 A1 | 11/2010 |
| WO | WO 2011/125056 A1 | 10/2011 |
| WO | WO 2013/050806 A1 | 4/2013 |
| WO | WO 2013/120492 A1 | 8/2013 |

OTHER PUBLICATIONS

Diaz, M., et al., "Hydrothermal pre-treatment of rapeseed straw," *Bioresource Technology*, Apr. 2010, pp. 2428-2435, vol. 101(7).

Dogaris, I., et al., "Hydrothermal processing and enzymatic hydrolysis of sorghum bagasse for fermentable carbohydrates production," *Bioresource Technology*, Dec. 2009, pp. 6543-6549, vol. 100(24).

Kabel, M., et al., "Effect of pretreatment severity on xylan solubility and enzymatic breakdown of the remaining cellulose from wheat straw," *Bioresource Technology*, Jul. 2007, pp. 2034-2042, vol. 98(10).

Larsen, J., et al., "The IBUS Process—Lignocellulosic Bioethanol Close to a Commercial Reality," *Chem. Eng. Technol.*, 2008, vol. 31(5), pp. 765-772.

Ouyang, J., et al., "Enhanced Enzymatic Conversion and Glucose Production Via Two-Step Enzymatic Hydrolysis of Corncob Residue from Xylo-Oligosaccharides Producer's Waste", *BioResources*, Jan. 2009, pp. 1586-1599, vol. 4(4).

(Continued)

*Primary Examiner* — Satyendra K Singh
(74) *Attorney, Agent, or Firm* — John Maldjian, Esq.; Stevens & Lee PC

(57) ABSTRACT

The invention relates, in general, to methods of processing Lignocellulosic biomass to fermentable sugars and to methods that rely on hydrothermal pretreatment. Xylose monomer yields comparable to those achieved using two-stage pretreatments can be achieved from soft Lignocellulosic biomass feedstocks by pretreating to very low severity in a single-stage pressurized hydrothermal pretreatment, followed by enzymatic hydrolysis to release xylose retained in the solid state. In some embodiments, pretreated biomass is separated into a solid fraction and a liquid fraction, the solid fraction subjected to enzymatic hydrolysis, and the separated liquid fraction subsequently mixed with the hydrolysed solid fraction.

20 Claims, 9 Drawing Sheets

(56) References Cited

OTHER PUBLICATIONS

Petersen, M., et al., "Optimization of hydrothermal pretreatment of wheat straw for production of bioethanol at low water consumption without addition of chemicals," Biomass and Bioenergy, May 2009, pp. 834-840, vol. 33(5).

Ramos, L. P., et al., "The use of enzyme recycling and the influence of sugar accumulation on cellulose hydrolysis by *Trichoderma* cellulases," *Enzyme and Microbial Technology*, Jan. 1993, pp. 19-25, vol. 15.

Taherzaeh, M., et al., "Pretreatment of Lignocellulosic Wastes to Improve Ethanol and Biogas Production: A Review," *Int.J.Mol. Sci.*, 2008, vol. 9, pp. 1621-1651.

Teherzadeh, M., et al., "Enzyme-Based Hydrolysis Processes For Ethanol From Lignocellulosic Materials: A Review," *BioResources*, 2007, vol. 2(4), pp. 707-738.

Thomsen, M., et al., "Preliminary Results on Optimization of Pilot Scale Pretreatment of Wheat Straw Used in Coproduction of Bioethanol and Electricity," *Applied Biochemistry and Biotechnology*, 2006, vol. 129-132, pp. 448-460.

Thygesen, A., et al., "Production of cellulose and hemicellulose-degrading enzymes by filamentous fungi cultivated on wet-oxidised straw," *Enzyme and Microbial Technology*, 2003, vol. 32(5), pp. 606-615.

Vegas, R., et al., "Hydrothermal processing of rice husks: effects of severity on product distribution," *Journal of Chemical Technology and Biotechnology*, Jul. 2008, pp. 965-972, vol. 83(7).

Yang, J., et al., "Three-stage hydrolysis to enhance enzymatic saccharification of steam-exploded corn stover," *Bioresource Technology*, Jul. 2010, pp. 4930-4935, vol. 101(13).

Yang, J., et al., "Three-stage enzymatic hydrolysis of steam-exploded corn stover at high substrate concentration," *Bioresource Technology*, Apr. 2011, pp. 4905-4908, vol. 102(7).

METHODS OF PROCESSING LIGNOCELLULOSIC BIOMASS USING SINGLE-STAGE AUTOHYDROLYSIS AND ENZYMATIC HYDROLYSIS WITH C5 BYPASS AND POST-HYDROLYSIS

CROSS-REFERENCE TO RELATED APPLICATIONS

This application is a continuation of U.S. patent application Ser. No. 17/329,960, filed May 25, 2021, which is a continuation of U.S. patent application Ser. No. 14/418,667, filed Jan. 30, 2015, issued as U.S. Pat. No. 11,118,203, which is a national stage filing under 35 U.S.C. 371 of PCT/DK2013/050256, filed Aug. 1, 2013, which International Application was published by the International Bureau in English on Feb. 6, 2014, and application claims priority from U.S. Provisional Application No. 61/678,130 filed Aug. 1, 2012, and Denmark Application No. PA 2012 70461, filed Aug. 1, 2012, which applications are hereby incorporated in their entirety by referenced in this application.

FIELD

The invention relates, in general, to methods of processing lignocellulosic biomass to fermentable sugars and, in particular, to methods that rely on hydrothermal pretreatment.

BACKGROUND

Historical reliance on petroleum and other fossil fuels has been associated with dramatic and alarming increases in atmospheric levels of greenhouse gases. International efforts are underway to mitigate greenhouse gas accumulation, supported by formal policy directives in many countries. One central focus of these mitigation efforts has been development of processes and technologies for utilization of renewable plant biomass to replace petroleum as a source of precursors for fuels and other chemical products. The annual growth of plant-derived biomass on earth is estimated to approximate $1 \times 10^{11}$ metric tons per year dry weight. See Lieth and Whittaker (1975). Biomass utilization is, thus, an ultimate goal in development of sustainable economy.

Fuel ethanol produced from sugar and starch based plant materials, such as sugarcane, root and grain crops, is already in wide use, with global production currently topping 73 billion liters per year. Ethanol has always been considered an acceptable alternative to fossil fuels, being readily usable as an additive in fuel blends or even directly as fuel for personal automobiles. However, use of ethanol produced by these "first generation" bioethanol technologies does not actually achieve dramatic reduction in greenhouse gas emission. The net savings is only about 13% compared with petroleum, when the total fossil fuel inputs to the final ethanol outputs are all accounted. See Farrell et al. (2006). Moreover, both economic and moral objections have been raised to the "first generation" bioethanol market. This effectively places demand for crops as human food into direct competition with demand for personal automobiles. And indeed, fuel ethanol demand has been associated with increased grain prices that have proved troublesome for poor, grain-importing countries.

Great interest has arisen in developing biomass conversion systems that do not consume food crops—so-called "second generation" biorefining, whereby bioethanol and other products can be produced from lignocellulosic biomass such as crop wastes (stalks, cobs, pits, stems, shells, husks, etc . . . ), grasses, straws, wood chips, waste paper and the like. In "second generation" technology, fermentable 6-carbon (C6) sugars derived primarily from cellulose and fermentable 5-carbon (C5) sugars derived from hemicellulose are liberated from biomass polysaccharide polymer chains by enzymatic hydrolysis or, in some cases, by pure chemical hydrolysis. The fermentable sugars obtained from biomass conversion in a "second generation" biorefinery can be used to produce fuel ethanol or, alternatively, other fuels such as butanol, or lactic acid monomers for use in synthesis of bioplastics, or many other products.

The total yield of both C5 and C6 sugars is a central consideration in commercialization of lignocellulosic biomass processing. In the case of ethanol production, and also production of lactate or other chemicals, it can be advantageous to combine both C5 and C6 sugar process streams into one sugar solution. Modified fermentive organisms are now available which can efficiently consume both C5 and C6 sugars in ethanol production. See e.g. Madhavan et al. (2012); Dumon et al. (2012); Hu et al. (2011); Kuhad et al. (2011); Ghosh et al. (2011); Kurian et al. (2010); Jojima et al. (2010); Sanchez et al. (2010); Bettiga et al. (2009); Matsushika et al. (2009).

Because of limitations of its physical structure, lignocellulosic biomass cannot be effectively converted to fermentable sugars by enzymatic hydrolysis without some pretreatment process. A wide variety of different pretreatment schemes have been reported, each offering different advantages and disadvantages. For review see Agbor et al. (2011); Girio et al. (2010); Alvira et al. (2010); Taherzadeh and Karimi (2008). From an environmental and "renewability" perspective, hydrothermal pretreatments are especially attractive. These utilize pressurized steam/liquid hot water at temperatures on the order of 160230° C. to gently melt hydrophobic lignin that is intricately associated with cellulose strands, to solubilize a major component of hemicellulose, rich in C5 sugars, and to disrupt cellulose strands so as to improve accessibility to productive enzyme binding. Hydrothermal pretreatments can be conveniently integrated with existing coal- and biomass-fired electrical power generation plants to efficiently utilize turbine steam and "excess" power production capacity.

In the case of hydrothermal processes, it is well known in the art, and has been widely discussed, that pretreatment must be optimized between conflicting purposes. On the one hand, pretreatment should ideally preserve hemicellulose sugar content, so as to maximize the ultimate yield of monomeric hemicellulose-derived sugars. Yet at the same time, pretreatment should sufficiently expose and pre-condition cellulose chains to susceptibility of enzymatic hydrolysis such that reasonable yields of monomeric cellulose-derived sugars can be obtained with minimal enzyme consumption. Enzyme consumption is also a central consideration in commercialization of biomass processing, which teeters on the verge of "economic profitability" in the context of "global market economies" as these are currently defined. Notwithstanding dramatic improvements in recent years, the high cost of commercially available enzyme preparations remains one of the highest operating costs in biomass conversion.

As hydrothermal pretreatment temperatures and reactor residence times are increased, a greater proportion of C5 sugars derived from hemicellulose is irretrievably lost due to chemical transformation to other substances, including furfural and products of condensation reactions. Yet higher temperatures and residence times are required in order to properly condition cellulose fibers for efficient enzymatic hydrolysis to monomeric 6-carbon glucose.

In the prior art, an often used parameter of hydrothermal pretreatment "severity" is "$R_o$," which is typically referred to as a log value. Ro reflects a composite measure of pretreatment temperature and reactor residence time according to the equation: $R_o = t * EXP[(T-100)/14.75]$ where t is residence time in minutes and T is reaction temperature in degrees centigrade. We have developed an alternative measure of pretreatment severity, "xylan number," which provides a negative linear correlation with classical log $R_o$, even at very low levels of "severity." Unlike $R_o$, which is a purely empirical description of pretreatment conditions, xylan number is a functionally significant physical parameter. Xylan number provides a measure of pretreatment degree that permits comparison of divergent biomass feedstocks, in terms of C5 recoveries, regardless of the Ro severity to which they have been subjected.

Whether hydrothermal pretreatment severity is expressed in terms of "xylan number" or "$R_o$," the optimization of pretreatment conditions for any given biomass feedstock inherently requires some compromise between demands for high monomeric C5 sugar yields from hemicellulose (low severity) and the demands for high monomeric C6 sugar yields from cellulose (high severity).

Hemicellulose-derived C5 sugars solubilized during hydrothermal pretreatment typically include a large fraction of xylo-oligomers, which strongly inhibit cellulase enzyme catalysis. See Shi et al. (2011); Quing and Wyman (2011); Quing et al. (2010). Other soluble byproducts of pretreatment, including acetic acid and phenolic compounds derived from solubilized lignin, are also known to inhibit cellulase enzyme catalysis. See Kothari and Lee (2011); Ximenes et al. (2010). The presence of effective levels of enzyme inhibitors increases enzyme consumption required to achieve a given degree of hydrolysis. Accordingly, "economic profitability" of commercial scale biomass conversion favors minimization of cellulase inhibition by soluble compounds derived from pretreatment.

A variety of different hydrothermal pretreatment strategies have been reported for maximizing sugar yields from both hemicellulose and cellulose and for minimizing xylo-oligomer inhibition of cellulase catalysis. In some cases, exogenous acids or bases are added in order to catalyse hemicellulose degradation (acid; pH<3.5) or lignin solubilisation (base; pH>9.0). In other cases, hydrothermal pretreatment is conducted using only very mild acetic acid derived from lignocellulose itself (pH 3.5-9.0). Hydrothermal pretreatments under these mild pH conditions have been termed "autohydrolysis" processes, because acetic acid liberated from hemicellulose esters itself further catalyses hemicellulose hydrolysis.

Acid catalysed hydrothermal pretreatments, known as "dilute acid" or "acid impregnation" treatments, typically provide high yields of C5 sugars, since comparable hemicellulose solubilisation can occur at lower temperatures in the presence of acid catalyst. Total C5 sugar yields after dilute acid pretreatment followed by enzymatic hydrolysis are typically on the order of 75% or more of what could theoretically be liberated from any given biomass feedstock. See e.g. Baboukaniu et al. (2012); Won et al. (2012); Lu et al. (2009); Jeong et al. (2010); Lee et al. (2008); Sassner et al. (2008); Thomsen et al. (2006); Chung et al. (2005).

Autohydrolysis hydrothermal pretreatments, in contrast, typically provide much lower yields of C5 sugars, since higher temperature pretreatment is required in the absence of acid catalyst. With the exception of autohydrolysis pretreatment conducted at commercially unrealistic low dry matter content, autohydrolysis treatments typically provide C5 sugar yields <40% theoretical recovery. See e.g. Diaz et al. (2010); Dogaris et al. (2009). C5 yields from autohydrolysis as high as 53% have been reported in cases where commercially unrealistic reactions times and extreme high enzyme doses were used. But even these very high C5 yields remain well beneath levels routinely obtained using dilute acid pretreatment. See e.g. Lee et al. (2009); Ohgren et al. (2007).

As a consequence of lower C5 yields obtained with autohydrolysis, most reports concerning hydrothermal pretreatment in commercial biomass conversion systems have focused on dilute acid processes. Hemicellulose-derived C5 sugar yields on the order of 85% have been achieved through use of so-called "two-stage" dilute acid pretreatments. In two-stage pretreatments, a lower initial temperature is used to solubilize hemicellulose, whereafter the C5-rich liquid fraction is separated. In the second stage, a higher temperature is used to condition cellulose chains. See e.g. Mesa et al. (2011); Kim et al. (2011); Chen et al. (2010); Jin et al. (2010); Monavari et al. (2009); Soderstrom et al. (2005); Soderstrom et al. (2004); Soderstrom et al. (2003); Kim et al. (2001); Lee et al. (1997); Paptheofanous et al. (1995). One elaborate "two-stage" dilute acid pretreatment system reported by the US National Renewable Energy Laboratory (NREL) claims to have achieved C5 yields on the order of 90% using corn stover as feedstock. See Humbird et al. (2011).

Xylo-oligomer inhibition of cellulase catalysis is avoided in dilute acid systems because hydrolysis of xylo-oligomers to monomeric xylose is catalysed by the added acid. The acid catalysed hydrolysis of xylo-oligomers also occurs within a separate process stream from that stream in which residual solids are subject to enzymatic hydrolysis.

Notwithstanding the lower C5 yields which it provides, autohydrolysis continues to offer competitive advantages over dilute acid pretreatments on commercial scale.

Most notable amongst the advantages of autohydrolysis processes is that the residual, unhydrolysed lignin has greatly enhanced market value compared with lignin recovered from dilute acid processes. First, the sulphuric acid typically used in dilute acid pretreatment imparts a residual sulphur content. This renders the resulting lignin unattractive to commercial power plants which would otherwise be inclined to consume sulphur-free lignin fuel pellets obtained from autohydrolysis as a "green" alternative to coal. Second, the sulfonation of lignin which occurs during sulphuric acid-catalysed hydrothermal pretreatments renders it comparatively hydrophilic, thereby increasing its mechanical water holding capacity. This hydrophilicity both increases the cost of drying the lignin for commercial use and also renders it poorly suited for outdoor storage, given its propensity to absorb moisture. So-called "techno-economic models" of NREL's process for lignocellulosic biomass conversion, with dilute acid pretreatment, do not even account for lignin as a saleable commodity—only as an internal source of fuel for process steam. See Hum bird et al. (2011). In contrast, the "economic profitability" of process schemes that rely on autohydrolysis include a significant contribution from robust sale of clean, dry lignin pellets. This is especially significant in that typical soft lignocellulosic biomass feedstocks comprise a large proportion of lignin, between 10 and 40% of dry matter content. Thus, even where process sugar yields from autohydrolysis systems can be diminished relative to dilute acid systems, overall "profitability" can remain equivalent or even better.

Autohydrolysis processes also avoid other well known disadvantages of dilute acid. The requirement for sulphuric acid diverges from a philosophical orientation favouring "green" processing, introduces a substantial operating cost for the acid as process input, and creates a need for elaborate waste water treatment systems and also for expensive anti-corrosive equipment.

Autohydrolysis is also advantageously scalable to modest processing scenarios. The dilute acid process described by NREL is so complex and elaborate that it cannot realistically be established on a smaller scale—only on a gigantic scale on the order of 100 tons of biomass feedstock per hour. Such a scale is only appropriate in hyper-centralized biomass processing scenarios. See Humbird et al. (2011). Hyper-centralized biomass processing of corn stover may well be appropriate in the USA, which has an abundance of genetically-engineered corn grown in chemically-enhanced hyper-production. But such a system is less relevant elsewhere in the world. Such a system is inappropriate for modest biomass processing scenarios, for example, on-site processing at sugar cane or palm oil or sorghum fields, or regional processing of wheat straw, which typically produces much less biomass per hectare than corn, even with genetic-engineering and chemical-enhancements.

Autohydrolysis systems, in contrast with dilute acid, are legitimately "green," readily scalable, and unencumbered by requirements for elaborate waste water treatment systems. It is accordingly advantageous to provide improved autohydrolysis systems, even where these may not be obviously advantageous over dilute acid systems in terms of sugar yields alone.

The problem of poor C5 monomer yields with autohydrolysis has generally driven commercial providers of lignocellulosic processing technology to pursue other approaches. Some "two-stage" pretreatment systems, designed to provide improved C5 yields, have been reported with autohydrolysis pretreatments. See WO2010/113129; US2010/0279361; WO 2009/108773; US2009/0308383; U.S. Pat. No. 8,057,639; US20130029406. In these "two stage" pretreatment schemes, some C5-rich liquid fraction is removed by solid/liquid separation after a lower temperature pretreatment, followed by a subsequent, higher temperature pretreatment of the solid fraction. Most of these published patent applications did not report actual experimental results. In its description of two-stage autohydrolytic pretreatment in WO2010/113129, Chemtex Italia reports a total of 26 experimental examples using wheat straw with an average C5 sugar recovery of 52%. These C5 recovery values do not distinguish between C5 recovery per se and monomer sugar yields, which is the substrate actually consumed in fermentation to ethanol and other useful products.

The introduction of a second pretreatment stage into a scheme for processing lignocellulosic biomass introduces additional complexities and costs. It is accordingly advantageous to substantially achieve the advantages of two-stage pretreatment using a simple single-stage autohydrolysis system.

We have discovered that, where single-stage autohydrolysis pretreatment is conducted to very low severity, unexpectedly high final C5 monomer yields of 60% theoretical yield and higher can be achieved following enzymatic hydrolysis, while still achieving reasonable glucose yields. Where biomass feedstocks are pretreated to xylan number 10% and higher, a large amount of the original xylan content remains within the solid fraction. Contrary to expectations, this very high residual xylan content can be enzymatically hydrolysed to monomer xylose, with high recovery, while sacrificing only a very small percentage of cellulose conversion to glucose.

At these very low severity levels, the production of soluble by-products that affect cellulase activity or fermentive organisms is kept so low that the pretreated material can be used directly in enzymatic hydrolysis, and subsequent fermentation, typically without requirement for any washing or other de-toxification step.

Inhibition of cellulase catalysis by xylo-oligomers or by other soluble products in the liquid fraction can be easily avoided in the process. A solid/liquid separation step following pretreatment generates a liquid fraction and a solid fraction. The C5-rich liquid fraction is maintained separately in "bypass" from the solid fraction during enzymatic hydrolysis. Following enzymatic hydrolysis of the solid fraction, liquid fraction is added to hydrolysate and subject to post-hydrolysis by remaining active xylanase enzymes. Xylo-oligomers within the liquid fraction are in this manner hydrolysed to xylose monomers only after cellulase activity is no longer necessary. The resulting combined hydrolysate and post-hydolysate comprising both C5 and C6 monomer sugars derived from both cellulose and hemicellulose can be directly fermented to ethanol by modified yeast.

BRIEF DESCRIPTION OF THE FIGURES

FIG. 2 shows the recovery of original hemicellulose sugars from wheat straw after pretreatment expressed as water insoluble solids (WIS) and water soluble solids (WSS) as a function of Xylan number.

FIG. 3 shows the recovery of original hemicellulose sugars after pretreatment as a function of Xylan number for wheat straw (PWS), corn stover (PCS), sugarcane bagasse (PSCB) and empty fruit bunches (PEFB).

FIG. 6 shows HPLC characterization of liquid fraction from wheat straw pretreated by Autohydrolysis to xylan number 11.5%.

FIG. 7 shows the hydrolysis profile showing conversions of C5 sugars to monomers during hydrolysis of solid fraction and after addition of liquid fraction at 96 hours expressed as % theoretical yield.

FIG. 8 shows the fermentation by yeast strain V1 from Terranol of steam pretreated wheat straw (xylan number >10%) that was previously hydrolyzed by Celic Ctec2 from Novozymes and used as combined liquid and solid fraction without de-toxification to remove fermentation inhibitors.

DETAILED DESCRIPTION OF EMBODIMENTS

Figure 1:
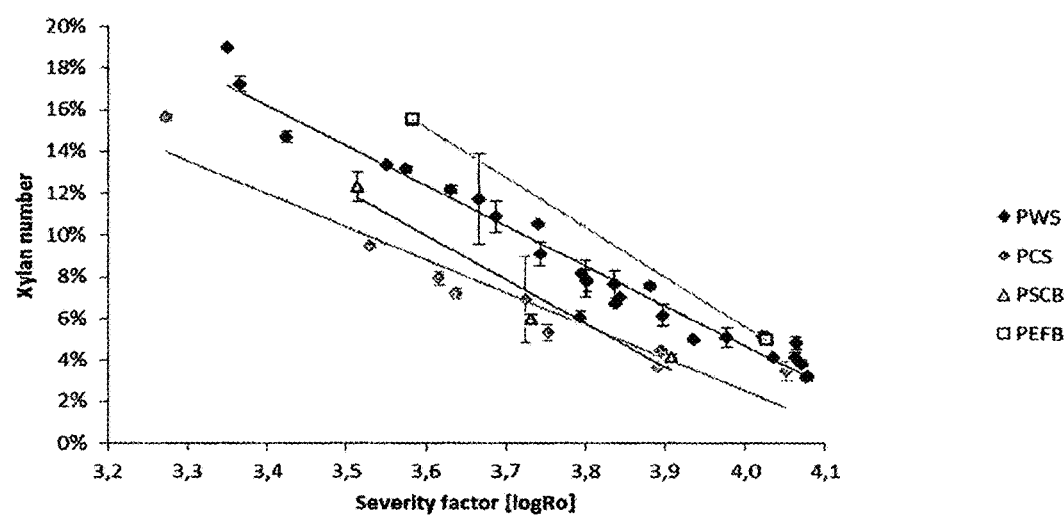
FIG. 1 shows xylan number as a function of pretreatment severity factor for soft lignocellulosic biomass feedstocks subject to autohydrolysis pretreatment. Soft lignocellulosic biomass feedstocks in the figure include pretreated wheat straw (PWS), corn stover (PCS), sugarcane bagasse (SCB) and empty fruit bunches from oil palm (PEFB).

In some embodiments the invention provides methods of processing lignocellulosic biomass comprising:
Providing soft lignocellulosic biomass feedstock,
Pretreating the feedstock at pH within the range 3.5 to 9.0 in a single-stage pressurized hydrothermal pretreatment to very low severity such that the pretreated biomass is characterized by having a xylan number of 10% or higher,
Separating the pretreated biomass into a solid fraction and a liquid fraction,
Hydrolysing the solid fraction with or without addition of supplemental water content using enzymatic hydrolysis catalysed by an enzyme mixture comprising endoglucanase, exoglucanase, B-glucosidase, endoxylanase, xylosidase and acetyl xylan esterase activities, and
Subsequently mixing the separated liquid fraction and the hydrolysed solid fraction, whereby xylo-oligomers in the liquid fraction are degraded to xylose monomers by the action of enzyme activities remaining within the hydrolysed solid fraction.

As used herein, the following terms have the following meanings:

"About" as used herein with reference to a quantitative number or range refers to +/−10% in relative terms of the number or range referred to.

"Auto hydrolysis" refers to a pretreatment process in which acetic acid liberated by hemicellulose hydrolysis during pretreatment further catalyzes hemicellulose hydrolysis, and applies to any hydrothermal pretreatment of lignocellulosic biomass conducted at pH between 3.5 and 9.0.

"Commercially available cellulase preparation optimized for lignocellulosic biomass conversion" refers to a commercially available mixture of enzyme activities that is sufficient to provide enzymatic hydrolysis of pretreated lignocellulosic biomass and that comprises endocellulase (endoglucanase), exocellulase (exoglucanase), endoxylanase, acetyl xylan esterase, xylosidase and B-glucosidase activities. The term "optimized for lignocellulosic biomass conversion" refers to a product development process in which enzyme mixtures have been selected and/or modified for the specific purpose of improving hydrolysis yields and/or reducing enzyme consumption in hydrolysis of pretreated lignocellulosic biomass to fermentable sugars.

Conducting pretreatment "at" a dry matter level refers to the dry matter content of the feedstock at the start of pressurized hydrothermal pretreatment. Pretreatment is conducted "at" a pH where the pH of the aqueous content of the biomass is that pH at the start of pressurized hydrothermal pretreatment.

"Dry matter," also appearing as DM, refers to total solids, both soluble and insoluble, and effectively means "non-water content." Dry matter content is measured by drying at 105° C. until constant weight is achieved.

"Fiber structure" is maintained to the extent that the average size of fiber fragments following pretreatment is >750 um.

"Hydrothermal pretreatment" refers to the use of water, either as hot liquid, vapor steam or pressurized steam comprising high temperature liquid or steam or both, to "cook" biomass, at temperatures of 120° C. or higher, either with or without addition of acids or other chemicals.

"Single-stage pressurized hydrothermal pretreatment" refers to a pretreatment in which biomass is subject to pressurized hydrothermal pretreatment in a single reactor configured to heat biomass in a single pass and in which no further pressurized hydrothermal pretreatment is applied following a solid/liquid separation step to remove liquid fraction from feedstock subject to pressurized hydrothermal pretreatment.

"Solid/liquid separation" refers to an active mechanical process whereby liquid is separated from solid by application of force through pressing, centrifugal or other force.

"Soft lignocellulosic biomass" refers to plant biomass other than wood comprising cellulose, hemicellulose and lignin.

"Solid fraction" and "Liquid fraction" refer to fractionation of pretreated biomass in solid/liquid separation. The separated liquid is collectively referred to as "liquid fraction." The residual fraction comprising considerable insoluble solid content is referred to as "solid fraction." A "solid fraction" will have a dry matter content and typically will also comprise a considerable residual of "liquid fraction."

"Theoretical yield" refers to the molar equivalent mass of pure monomer sugars obtained from polymeric cellulose, or from polymeric hemicellulose structures, in which constituent monomeric sugars may also be esterified or otherwise substituted. "C5 monomer yields" as a percentage of theoretical yield are determined as follows: Prior to pretreatment, biomass feedstock is analysed for carbohydrates using the strong acid hydrolysis method of Sluiter et al. (2008) using an HPLC column and elution system in which galactose and mannose co-elute with xylose. Examples of such systems include a REZEX™ Monossacharide H+ column from Phenomenex and an AMINEX HPX 87C™ column from Bio-rad. During strong acid hydrolysis, esters and acid-labile substitutions are removed. Except as otherwise specified, the total quantity of "Xylose" +Arabinose determined in the un-pretreated biomass is taken as 100% theoretical C5 monomer recovery, which can be termed collectively "C5 monomer recovery." Monomer sugar determinations are made using HPLC characterization based on standard curves with purified external standards. Actual C5 monomer recovery is determined by HPLC characterization of samples for direct measurement of C5 monomers, which are then expressed as a percent of theoretical yield.

"Xylan number" refers to a characterization of pretreated biomass determined as follows: Pretreated biomass is subject to solid/liquid separation to provide a solid fraction at about 30% total solids and a liquid fraction. This solid fraction is then partially washed by mixing with 70° C. water in the ratio of total solids (DM) to water of 1:3 wt:wt. The solid fraction washed in this manner is then pressed to about 30% total solids. Xylan content of the solid fraction washed in this manner is determined using the method of A. Sluiter, et al., "Determination of structural carbohydrates and lignin in biomass," US National Renewable Energy Laboratory (NREL) Laboratory Analytical Procedure (LAP) with issue date Apr. 25, 2008, as described in Technical Report NREL/TP-510-42618, revised April 2008. An HPLC column and elution system is used in which galactose and mannose co-elute with xylose. Examples of such systems include a REZEX™ Monossacharide H+ column from Phenomenex and an AMINEX HPX 87C™ column from Biorad. This measurement of xylan content as described will include some contribution of soluble material from residual liquid fraction that is not washed out of solid fraction under these conditions. Accordingly, "xylan number" provides a "weighted combination" measurement of residual xylan content within insoluble solids and of soluble xylose and xylo-oligomer content within the "liquid fraction."

Any suitable soft lignocellulosic biomass may be used, including biomasses such as at least wheat straw, corn stover, corn cobs, empty fruit bunches, rice straw, oat straw, barley straw, canola straw, rye straw, sorghum, sweet sorghum, soybean stover, switch grass, Bermuda grass and other grasses, bagasse, beet pulp, corn fiber, or any combinations thereof. Lignocellulosic biomass may comprise other lignocellulosic materials such as paper, newsprint, cardboard, or other municipal or office wastes. Lignocellulosic biomass may be used as a mixture of materials originating from different feedstocks, may be fresh, partially dried, fully dried or any combination thereof. In some embodiments, methods of the invention are practiced using at least about 10 kg biomass feedstock, or at least 100 kg, or at least 500 kg.

Lignocellulosic biomass comprises crystalline cellulose fibrils intercalated within a loosely organized matrix of hemicellulose and sealed within an environment rich in hydrophobic lignin. While cellulose itself comprises long, straight chain polymers of D-glucose, hemicellulose is a heterogeneous mixture of short, branched-chain carbohydrates including monomers of all the 5-carbon aldopentoses (C5 sugars) as well as some 6-carbon (C6) sugars including glucose and mannose. Lignin is a highly heterogeneous polymer, lacking any particular primary structure, and comprising hydrophobic phenylpropanoid monomers.

Suitable lignocellulosic biomass typically comprises cellulose in amounts between 20 and 50% of dry mass prior to pretreatment, lignin in amounts between 10 and 40% of dry mass prior to pretreatment, and hemicellulose in amounts between 15 and 40%.

In some embodiments, biomass feedstocks may be subject to particle size reduction and/or other mechanical processing such as grinding, milling, shredding, cutting or other processes prior to hydrothermal pretreatment. In some embodiments, biomass feedstocks may be washed and/or leached of valuable salts prior to pressurized pretreatment, as described in Knudsen et al. (1998). In some embodiments feedstocks may be soaked prior to pressurized pretreatment at temperatures up to 99° C.

In some embodiments the feedstock is first soaked in an aqueous solution prior to hydrothermal pretreatment. In some embodiments, it can be advantageous to soak the feedstock in an acetic acid containing liquid obtained from a subsequent step in the pretreatments, as described in U.S. Pat. No. 8,123,864. It is advantageous to conduct treatment at the highest possible dry matter content, as described in U.S. Ser. No. 12/935,587. Conducting pretreatment at high dry matter avoids expenditure of process energy on heating of unnecessary water. However, some water content is required to achieve optimal eventual sugar yields from enzymatic hydrolysis. Typically it is advantageous to pretreat biomass feedstocks at or close to their inherent water holding capacity. This is the level of water content that a given feedstock will attain after soaking in an excess of water followed by pressing to the mechanical limits of an ordinary commercial screw press—typically between 30 and 45% DM. In some embodiments, hydrothermal pretreatment is conducted at DM content at least 35%. It will be readily understood by one skilled in the art that DM content may decrease during hydrothermal pretreatment as some water content is added during heating. In some embodiments, feedstocks are pretreated at DM content at least 20%, or at least 25%, or at least 30%, or at least 40%, or 40% or less, or 35% or less, or 30% or less.

In some embodiments, soaking/wetting with an aqueous solution can serve to adjust pH prior to pretreatment to the range of between 3.5 and 9.0, which is typically advantageous for autohydrolysis. It will be readily understood that pH may change during pretreatment, typically to more acidic levels as acetic acid is liberated from solubilized hemicellulose.

In some embodiments, hydrothermal pretreatment is conducted without supplemental oxygen as required for wet oxidation pretreatments, or without addition of organic solvent as required for organosolv pretreatment, or without use of microwave heating as required for microwave pretreatments. In some embodiments, hydrothermal pretreatment is conducted at temperatures of 140° C. or higher, or at 150° C. or higher, or at 160° C. or higher, or between 160 and 200° C., or between 170 and 190° C., or at 180° C. or lower, or at 170° C. or lower.

In some embodiments, some C5 content may be removed by a soaking step prior to pressurized pretreatment. In some embodiments, the single reactor may be configured to heat biomass to a single target temperature. Alternatively, the single reactor may be configured to affect a temperature gradient within the reactor such that biomass is exposed, during a single passage, to more than one temperature region. In some embodiments, it may be advantageous to partially remove some solubilized biomass components from within the pressurized reactor during the course of pretreatment.

Suitable hydrothermal pretreatment reactors typically include most pulping reactors known from the pulp and paper industry. In some embodiments, hydrothermal pretreatment is administered by steam within a reactor pressurized to 10 bar or lower, or to 12 bar or lower, or to 4 bar or higher, or 8 bar or higher, or between 8 and 18 bar, or between 18 and 20 bar. In some embodiments, the pretreatment reactor is configured for a continuous inflow of feedstock.

In some embodiments, wetted biomass is conveyed through the reactor, under pressure, for a certain duration or "residence time." Residence time is advantageously kept brief to facilitate higher biomass throughput. However, the pretreatment severity obtained is determined both by temperature and also by residence time. Temperature during hydrothermal pretreatment is advantageously kept lower, not only because methods of the invention seek to obtain a very low pretreatment severity, but also because lower temperatures can be accomplished using lower steam pressures. To the extent that pretreatment temperature can be at levels of 180° C. or lower, and accordingly, saturated steam pressures kept to 10 bar or lower, lower tendency for corrosion is experienced and much lower grade pressure fittings and steel compositions may be used, which reduces plant capital costs. In some embodiments, the reactor is configured to heat biomass to a single target temperature between 160 and 200° C., or between 170 and 190° C. Residence times in some embodiments are less than 60, or less than 30, or less than 20, or less than 15, or less than 14, or less than 13, or less than 12, or less than 10, or less than 8, or less than 5 minutes.

Biomass feedstocks may be loaded from atmospheric pressure into a pressurized reactor by a variety of means. In some embodiments, a sluice-type "particle pump" system may be used to load biomass feedstocks, such as the system described in U.S. Ser. No. 13/062,522. In some embodiments, it may be advantageous to load a pretreatment reactor using a so-called "screw plug" feeder.

Pretreated biomass may be unloaded from a pressurized reactor by a variety of means. In some embodiments, pretreated biomass is unloaded in such manner as to preserve the fiber structure of the material. Preserving the fiber structure of the pretreated biomass is advantageous because this permits the solid fraction of the pretreated material to be pressed during solid/liquid separation to comparatively high dry matter levels using ordinary screw press equipment, and thereby avoiding the added expense and complexity of membrane filter press systems.

Fiber structure can be maintained by removing the feedstock from the pressurized reactor in a manner that is non-explosive. In some embodiments, non-explosive removal may be accomplished and fiber structure thereby maintained using a sluice-type system, such as that described in U.S. Ser. No. 13/043,486. In some embodiments, non-explosive removal may be accomplished and fiber structure thereby maintained using a hydrocyclone removal system, such as those described in U.S. Ser. No. 12/996,392.

In some embodiments, pretreated biomass can be removed from a pressurized pretreatment reactor using "steam explosion," which involves explosive release of the pretreated material. Steam-exploded, pretreated biomass does not retain its fiber structure and accordingly requires more elaborate solid/liquid separation systems in order to achieve dry matter content comparable to that which can be achieved using ordinary screw press systems with pretreated biomass that retains its fiber structure.

The biomass feedstock is pretreated to very low severity, such that the pretreated biomass is characterized by having a xylan number of 10% or higher. In some embodiments, the biomass is pretreated to a xylan number of 11% or higher, or 12% or higher, or 13% or higher, or 14% or higher, or 15% or higher, or 16% or higher, or 17% or higher. The parameter "xylan number" refers to a composite measurement that reflects a weighted combination of both residual xylan content remaining within insoluble solids and also the concentration of soluble xylose and xylo-oligomers within the liquid fraction. At lower Ro severity, xylan number is higher. Thus, the highest xylan number refers to the lowest pretreatment severity. Xylan number provides a negative linear correlation with the conventional severity measure log $R_o$ even to very low severity, where residual xylan content within insoluble solids is 10% or higher.

Xylan number is particularly useful as a measure of pretreatment severity in that different pretreated biomass feedstocks having equivalent xylan number exhibit equivalent C5 monomer recovery. In contrast, conventional Ro severity is simply an empirical description of pretreatment conditions, which does not provide a rational basis for comparisons between different biomass feedstocks. For example, single-stage autohydrolysis to severity log $R_o=3.75$ provides pretreated sugar cane bagasse and corn stover having a xylan number of between 6-7%, while with typical wheat straw strains, the resulting xylan number of pretreated feedstock is about 10%.

It is advantageous that biomass feedstocks be pretreated to very low severity wherein xylan number of the pretreated feedstock is 10% or greater. This very low severity level corresponds to a process in which the total hemicellulose content of the feedstock before pretreatment that is either solubilized or irretrievably lost during pretreatment is minimized. At xylan number 10% and higher, with typical strains of wheat straw, sugar cane bagasse, sweet sorghum bagasse, corn stover, and empty fruit bunches (from oil palm), at least 60% of the original C5 content of the feedstock can be recovered after single-stage autohydrolysis pretreatment, where both xylan in the solid fraction and also soluble xylose and xylo-oligomers in the liquid fraction are accounted for.

We have unexpectedly discovered that high final C5 monomer yields of at least 55% theoretical, or at least 60%, or at least 65%, can be obtained without appreciable loss of C6 monomer yields after enzymatic hydrolysis of feedstocks pretreated to very low severity by single-stage autohydrolysis. At very low severity levels, a large fraction of the feedstock's hemicellulose content remains within the solid fraction after pretreatment, where it can subsequently be hydrolysed to C5 monomers with high recovery using enzymatic hydrolysis.

It should be noted that reports concerning "xylose recovery" are often expressed in terms that are not comparable to the xylose recoveries reported here. For example, Ohgren et al. (2007) and Lee et al. (2009) report high xylose recoveries. But these values refer only to xylose recovery from pretreated biomass, not expressed as a percentage of the original hemicellulose content of the feedstock prior to pretreatment. Or for example WO2010/113129 refers to hemicellulose recovery as a percentage of hemicellulose content of the feedstock prior to pretreatment, but does not specify the monomer yield, which is invariable smaller than the total hemicellulose recovery.

Another startling feature of biomass that has been pretreated by single-stage autohydrolysis to very low severity levels is that the concentrations of pretreatment by-products that serve as inhibitors of fermentive organisms are kept to very low levels. As a consequence, it is typically possible to use hydrolysed biomass obtained by methods of the invention directly in fermentations, without requirement for any washing or other de-toxification step.

As is well known in the art, autohydrolysis hydrothermal pretreatment typically produces a variety of soluble by-products which act as "fermentation inhibitors," in that these inhibit growth and/or metabolism of fermentive organisms. Different fermentation inhibitors are produced in different amounts, depending on the properties of the lignocellulosic feedstock and on the severity of pretreatment. See Klinke et al. (2004). At least three categories of fermentation inhibitors are typically formed during autohydrolysis pretreatment: (1) furans, primarily 2-furfural and 5-HMF (5 hydroxymethylfurfural) which are degradation products from mono- or oligo-saccharides; (2) monomeric phenols, which are degradation products of the lignin structure; and (3) small organic acids, primarily acetic acid, which originate from acetyl groups in hemicelluloses, and lignin. The mixture of different inhibitors has been shown to act synergistically in bioethanol fermentation using yeast strains, see e.g. Palmquist et al. (1999), and, also, using ethanolic

*Escherichia coli*, see e.g. Zaldivar et al. (1999). In some embodiments, it can be advantageous to subject pretreated biomass to flash evaporation, using methods well known in the art, in order to reduce levels of volatile inhibitors, most notably furfural. Using autohydrolysis with typical strains of biomass feedstocks such as wheat straw, sweet sorghum bagasse, sugar cane bagasse, corn stover, and empty fruit bunches, pretreated to xylan number 10% or higher, in our experience only acetic acid and furfural levels are potentially inhibitory of fermentive organisms. Where biomass feedstocks are pretreated at DM 35% or higher to xylan number 10% or higher, and where solid fraction is subsequently hydrolysed enzymatically at 25% or lower DM, with added water to adjust DM but without washing steps, furfural levels in the hydrolysate can typically be kept under 3 g/kg and acetic acid levels beneath 9 g/kg. These levels are typically acceptable for yeast fermentations using specialized strains. During enzymatic hydrolysis, some additional acetic acid is released from degradation of hemicellulose in the solid fraction. In some embodiments, it may be advantageous to remove some acetic acid content from liquid fraction and/or hydrolysed solid fraction using electrodialysis or other methods known in the art.

Different feedstocks can be pretreated using single-stage autohydrolysis to xylan number 10% or greater by a variety of different combinations of reactor residence times and temperatures. One skilled in the art will readily determine through routine experimentation an appropriate pretreatment routine to apply with any given feedstock, using any given reactor, and with any given biomass reactor-loading and reactor-unloading system. Where feedstocks are pretreated using a continuous reactor, loaded by either a sluice-system or a screw-plug feeder, and unloaded by either a "particle pump" sluice system or a hydrocyclone system, very low severity of 10% or greater xylan number can be achieved using typical strains of wheat straw or empty fruit bunches by a temperature of 180° C. and a reactor residence time of 24 minutes. For typical strains of corn stover, sugar cane bagasse, and sweet sorghum bagasse, very low severity of 10% or greater xylan number can typically be achieved using a temperature of 180° C. and a reactor residence time of 12 minutes, or using a temperature of 175° C. and a reactor residence time of 17 minutes. It will be readily understood by one skilled in the art that residence times and temperatures maybe adjusted to achieve comparable levels of $R_o$ severity.

Following pretreatment, pretreated biomass is separated into a solid fraction and a liquid fraction by a solid/liquid separation step. It will be readily understood that "solid fraction" and "liquid fraction" may be further subdivided or processed. In some embodiments, biomass may be removed from a pretreatment reactor concurrently with solid/liquid separation. In some embodiments, pretreated biomass is subject to a solid/liquid separation step after it has been unloaded from the reactor, typically using a simple and low cost screw press system, to generate an solid fraction and a liquid fraction. Cellulase enzyme activities are inhibited by liquid fraction, most notably due to xylo-oligomer content but possibly also due to phenol content and/or other compounds not yet identified. It is accordingly advantageous to achieve the highest practicable levels of dry matter content in the solid fraction or, alternatively, to remove the highest practicable amount of dissolved solids from the solid fraction. In some embodiments, solid/liquid separation achieves a solid fraction having a DM content of at least 40%, or at least 45%, or at least 50%, or at least 55%. Solid/liquid separation using ordinary screw press systems can typically achieve DM levels as high as 50% in the solid fraction, provided the biomass feedstock has been pretreated in such manner that fiber structure is maintained. In some embodiments, it may be advantageous to incur higher plant capital expenses in order to achieve more effective solid/liquid separation, for example, using a membrane filter press system. In some embodiments, dissolved solids can be removed from a solid fraction by serial washing and pressing or by displacement washing techniques known in the pulp and paper art. In some embodiments, either by solid/liquid separation directly, or by some combination of washing and solid/liquid separation, the dissolved solids content of the solid fraction is reduced by at least 50%, or at least 55%, or at least 60%, or at least 65%, or at least 70%, or at least 75%.

Enzymatic hydrolysis of feedstocks pretreated to xylan number 10% or higher can typically be conducted with commercially reasonable enzyme consumption, without requirement for specific washing or de-toxification steps, where the solid fraction is pressed to at least 40% DM, or where dissolved solids content of the solid fraction is reduced by at least 50%.

The liquid fraction obtained from solid/liquid separation is maintained separately from solid fraction during enzymatic hydrolysis of the solid fraction. We term this temporary separation "C5 bypass." Liquid fraction obtained from soft lignocellulosic biomass feedstocks such as typical strains of wheat straw, sugar cane bagasse, sweet sorghum bagasse, corn stover, and empty fruit bunches pretreated by single-stage autohydrolysis to xylan number 10% or higher typically comprise a small component of C6 monomers (1×), primarily glucose with some other sugars; a larger component of soluble C6 oligomers (about 2×-7×); a larger component of C5 monomers (about 4×-8×), primarily xylose with some arabinose and other sugars; and a much larger component of soluble xylo-oligomers (about 18×-30×). Soluble xylo-oligomers typically include primarily xylohexose, xylopentose, xylotetraose, xylotriose and xylobiose with some higher chain oligomers.

The solid fraction is subject to enzymatic hydrolysis using a mixture of enzyme activities. As will be readily understood by one skilled in the art, the composition of enzyme mixtures suitable for practicing methods of the invention may vary within comparatively wide bounds. Suitable enzyme preparations include commercially available cellulase preparations optimized for lignocellulosic biomass conversion. Selection and modification of enzyme mixtures during optimization may include genetic engineering techniques, for example such as those described by Zhang et al. (2006) or by other methods known in the art. Commercially available cellulase preparations optimized for lignocellulosic biomass conversion are typically identified by the manufacturer and/or purveyor as such. These are typically distinct from commercially available cellulase preparations for general use or optimized for use in production of animal feed, food, textiles detergents or in the paper industry. In some embodiments, a commercially available cellulase preparation optimized for lignocellulosic biomass conversion is used that is provided by GENENCOR™ and that comprises exoglucanases, endoglucanases, endoxylanases, xylosidases, acetyl xylan esterases and beta glucosidases isolated from fermentations of genetically modified *Trichoderma reesei*, such as, for example, the commercial cellulase preparation sold under the trademark ACCELLERASE TRIO™. In some embodiments, a commercially available cellulase preparation optimized for lignocellulosic biomass conversion is used that is provided by NOVOZYMES™ and that comprises exoglucanases, endoglucanases, endoxylanases, xylosidases, acetyl xylan esterases and beta glucosidases, such as, for example, the commercial cellulase preparations sold under either of the trademarks CELLIC CTEC2™ or CELLIC CTEC3™.

The enzyme activities represented in three commercially available cellulase preparation optimized for lignocellulosic biomass conversion were analysed in detail. Each of these three preparations, ACCELLERASE TRIO™ from GENENCOR™ and CELLIC CTEC2™ and CELLIC CTEC3™ from NOVOZYMES™, was shown to be effective at enzyme dose levels within the manufacturers' suggested range, in providing combined C5/C6 wheat straw hydrolysate prepared according to methods of the invention in which C5 monomer yields were at least 60% and cellulose C6 conversion yields were at least 60%. For each of these commercial cellulase preparations, levels of twelve different enzyme activities were characterized and expressed per gram protein. Experimental details are provided in Example 8. Results are shown in Table 1.

Divne, C., et al. (1994); Martinez, D., et al. (2008). Commercial cellulase preparations typically also include alpha-arabinofuranosidase and acetyl xylan esterase activities. See e.g. Vinzant, T., et al. (2001).

An optimized mixture of enzyme activities in relative proportions that differ from the proportions presented in mixtures naturally secreted by wild type organisms has previously been shown to produce higher sugar yields. See Rosgaard et al. (2007). Indeed, it is has been suggested that optimizations of enzyme blends including as many as 16 different enzyme proteins can be advantageously determined separately for any given biomass feedstock subject to any given pretreatment. See Billard, H., et al. (2012); Banerjee, G., et al. (2010). As a commercial practicality, however, commercial enzyme providers typically seek to produce the smallest practicable number of different enzyme blends, in order that economies of scale can be obtained in large-scale production.

In some embodiments, it can be advantageous to supplement a commercially available cellulase preparation opti-

TABLE 1

Selected activity measurements in commercial cellulase preparations optimized for lignocellulosic biomass conversion.

|  | CTEC3 | Activity ACTrio | CTEC2 | Substrate | Unit definition (formation) |
|---|---|---|---|---|---|
| CBH I | 454 ± 2.5 U/g | 171 ± 0.4 U/g | 381 ± 21 U/g | MeUmb-3- cellobioside | 1 μmole MeUmd equivalent/min |
| CBH II* | Not measurable | Not measurable | Not measurable |  |  |
| Endo-1,4-β-glucanase | 466 ± 31 U/g | 149 ± 21 U/g | 173 ± 15 U/g | Avicel PH-101 | 1 μmole glucose equivalent/min. |
| β-glucosidase | 3350 ± 75 U/g | 891 ± 60 U/g | 2447 ± 70 U/g | Cellobiose | 2 μmole glucose/min. (Conversion of 1 μmole cellobiose/min) |
| Endo-1,4-β-xylanase | 278 ± 10 U/g | 799 ± 55 U/g | 306 ± 41 U/g | WEAX (medium visc.) | 1 μmole glucose equivalent/min. |
| β-xylosidase | 279 ± 7.0 U/g | 431 ± 22 U/g | 87 ± 0.2 U/g | WEAX (medium visc.) | 1 μmole xylose/min. |
| β-L-arabinofuranosidase | 20 ± 1.0 U/g | 9.4 ± 0.4 U/g | 12 ± 0.1 U/g | WEAX (medium visc.) | 1 μmole arabinose/min. |
| Laccase | No activity | No activity | No activity | Syringaldazine | — |
| Amyloglucosidase (AMG) | 18 ± 3.6 U/g | 29 ± 0.1 U/g | 18 ± 1.5 U/g | Corn starch (soluble) | 1 μmole glucose/min. |
| o-amylase | 2.7 ± 0.1 U/g | 3.4 ± 0.5 U/g | 4.7 ± 1.4 U/g | Corn starch (soluble) | 1 μmole glucose equivalent/min. |
| Acetyl xylan esterase | $3.8 \cdot 10^{-3} \pm 9 \cdot 10^{-5}$ U/g | $3.1 \cdot 10^{-4} \pm 1 \cdot 10^{-4}$ U/g | $4.2 \cdot 10^{-3} \pm 4.2 \cdot 10^{-4}$ U/g | pNP-acetate | 1 μmole pNP equivalent min. |
| Ferulic acid esterase | No activity | No activity | No activity | Methyl ferulate | — |

In some embodiments, enzyme preparations may be used that have similar relative proportions as those exhibited by the commercial preparations described in Table 1 between any of the endoglucanase, exoglucanase, B-glucosidase, endoxylanase, xylosidase and/or acetyl xylan esterase activities.

Enzyme mixtures that are effective to hydrolyse lignocellulosic biomass can alternatively be obtained by methods well known in the art from a variety of microorganisms, including aerobic and anaerobic bacteria, white rot fungi, soft rot fungi and anaerobic fungi. See e.g. Singhania et al. (2010). Organisms that produce cellulases typically secrete a mixture of different enzymes in appropriate proportions so as to be suitable for hydrolysis of lignocellulosic substrates. Preferred sources of cellulase preparations useful for conversion of lignocellulosic biomass include fungi such as species of *Trichoderma, Penicillium, Fusarium, Humicola, Aspergillus* and *Phanerochaete*.

One fungus species in particular, *Trichoderma reesei*, has been extensively studied. Wild type *Trichoderma reesei* secretes a mixture of enzymes comprising two exocellulases (cellobiohydrolases) with respective specificities for reducing and non-reducing ends of cellulose chains, at least five different endocellulases having differing cellulose recognition sites, two B-glucosidases as well as a variety of endoxylanases and exoxylosidases. See Rouvinen, J., et al. (1990);

mized for lignocellulosic biomass conversion with one or more additional or supplemental enzyme activities. In some embodiments, it may be advantageous simply to increase the relative proportion of one or more component enzymes present in the commercial preparation. In some embodiments, it may be advantageous to introduce specialized additional activities. For example, in practicing methods of the invention using any given biomass feedstock, particular unhydrolysed carbohydrate linkages may be identified that could be advantageously hydrolysed through use of one or more supplemental enzyme activities. Such unhydrolysed linkages may be identified through characterization of oligomeric carbohydrates, using methods well known in the art, in soluble hydrolysates or in insoluble unhydrolysed residual. Unhydrolysed linkages may also be identified through comprehensive microarray polymer profiling, using monoclonal antibodies directed against specific carbohydrate linkages, as described by Nguema-Ona et al. (2012). In some embodiments it can be advantageous to supplement a commercially available cellulase preparation optimized for lignocellulosic biomass conversion using any one or more of additional endoxylanase, B-glucosidase, mannanase, glucouronidase, xylan esterase, amylase, xylosidase, glucouranyl esterase, or arabinofuranosidase.

In some embodiments, it can alternatively be advantageous to produce enzymes on-site at a lignocellulosic biomass processing facility, as described by Humbird et al. (2011). In some embodiments, a commercially available cellulase preparation optimized for lignocellulosic biomass conversion may be produced on-site, with or without customized supplementation of specific enzyme activities appropriate to a particular biomass feedstock.

In some embodiments, whether or not a commercially available cellulase preparations optimized for lignocellulosic biomass conversion is used, and whether or not enzymes are produced on-site at a biomass processing plant, advantages of the invention can be obtained using soft lignocellulosic biomass feedstocks subject to autohydrolysis pretreatment to very low severity xylan number 10% or greater using an enzyme mixture that comprises the following: (1) Exocellulase (cellobiohydrolase) activities (EC 3.2.1.91), optionally including at least two enzymes with specificities for reducing and non-reducing ends of cellulose chains; (2) endocellulase activity (EC 3.2.1.4); (3) B-glucosidase activity (EC 3.2.1.21); (4) B-1,4 endoxylanase activity (EC 3.2.1.8); (5) acetyl xylan esterase activity (EC 3.1.1.72); and optionally (6) B-1,3 xylosidase activity (EC 3.2.1.72); and optionally (7) B-1,4 xylosidase activity (EC 3.2.1.37); and optionally (8) alpha 1,3 and/or alpha 1, 5 arabinofuranosidase activity (EC 3.2.1.23). In some embodiments, the enzyme mixture is further characterized by having relative proportions of enzyme activities as follows: 1 FPU cellulase activity is associated with at least 30 CMC U endoglucanase activity and with at least at least 28 pNPG U beta glucosidase activity and with at least 50 ABX U endoxylanase activity. It will be readily understood by one skilled in the art that CMC U refers to carboxymethycellulose units, where one CMC U of activity liberates 1 umol of reducing sugars (expressed as glucose equivalents) in one minute under specific assay conditions of 50° C. and pH 4.8; that pNPG U refers to pNPG units, where one pNPG U of activity liberates 1 umol of nitrophenol per minute from para-nitrophenyl-B-D-glucopyranoside at 50° C. and pH 4.8; and that ABX U refers to birchwood xylanase units, where one ABX U of activity liberates 1 umol of xylose reducing sugar equivalent in one minute at 50° C. and pH 5.3. It will be further readily understood by one skilled in the art that FPU refers to "filter paper units," which provides a measure of total cellulase activity including any mixture of different cellulase enzymes. As used herein, FPU refers to filter paper units as determined by the method of Adney, B. and Baker, J., Laboratory Analytical Procedure #006, "Measurement of cellulase activity", Aug. 12, 1996, the USA National Renewable Energy Laboratory (NREL).

In some embodiments the enzyme mixture may further include any one or more of mannosidases (EC 3.2.1.25), a-D-galactosidases (EC 3.2.1.22), a-L-arabinofuranosidases (EC 3.2.1.55), a-D-glucuronidases (EC 3.2.1.139), cinnamoyl esterases (EC 3.1.1.-), or feruloyl esterases (EC 3.1.1.73).

One skilled in the art will readily determine, through routine experimentation, an appropriate dose level of any given enzyme preparation to apply, and an appropriate duration for enzymatic hydrolysis. It is generally advantageous to maintain lower enzyme dose levels, so as to minimize enzyme costs. In some embodiments, it can be advantageous to use a high enzyme dose. In practicing methods of the invention, one skilled in the art can determine an economic optimisation of enzyme dose in consideration of relevant factors including local biomass costs, market prices for product streams, total plant capital costs and amortization schemes, and other factors. In embodiments where a commercially available cellulase preparation optimized for lignocellulosic biomass conversion is used, a general dose range provided by manufacturers can be used to determine the general range within which to optimize. Hydrolysis duration in some embodiments is at least 48 hours, or at least 64 hours, or at least 72 hours, or at least 96 hours, or for a time between 24 and 150 hours.

As is well known in the art, cellulase catalysis is more efficient where hydrolysis is conducted at low dry matter content. Higher solids concentration effectively inhibits cellulase catalysis, although the precise reasons for this well known effect are not fully understood. See e.g. Kristensen et al. (2009).

In some embodiments, it may be advantageous to conduct hydrolysis at very high DM>20%, notwithstanding some resulting increase in enzyme consumption. It is generally advantageous to conduct hydrolysis at the highest practicable dry matter level, both in order to minimize water consumption and waste water treatment requirements. It is additionally advantageous in fermentation systems to use the highest practicable sugar concentrations. Higher sugar concentrations are produced where hydrolysis is conducted at higher dry matter levels. One skilled in the art will readily determine, through routine experimentation, a DM level at which to conduct enzymatic hydrolysis that is appropriate to achieve given process goals, for any given biomass feedstock and enzyme preparation. In some embodiments, enzymatic hydrolysis of the solid fraction may be conducted at 15% DM or greater, or at 16% DM or greater, or at 17% DM or greater, or at 18% DM or greater or at 19% DM or greater, or at 20% DM or greater, or at 21% DM or greater, or at 22% DM or greater, or at 23% DM or greater, or at 25% DM or greater, or at 30% DM or greater, or at 35% DM or greater.

In some embodiments, solid fraction is recovered from solid/liquid separation at 40% DM or greater, but additional water content is added so that enzymatic hydrolysis may be conducted at lower DM levels. It will be readily understood that water content may be added in the form of fresh water, condensate or other process solutions with or without additives such as polyethylene glycol (PEG) of any molecular weight or surfactants, salts, chemicals for pH adjustment such as ammonia, ammonium hydroxide, calcium hydroxide, or sodium hydroxide, anti-bacterial or anti-fungal agents, or other materials.

After the solid fraction has been enzymatically hydrolysed to a desired degree of conversion, the liquid fraction, which has been maintained in C5 bypass, is mixed with the hydrolysate mixture for post-hydrolysis. In some embodiments, all of the recovered liquid fraction may be added at one time, while in other embodiments, some component of the liquid fraction may be removed and/or liquid fraction may be added incrementally. In some embodiments, prior to mixing with liquid fraction, the solid fraction is hydrolysed to at least 50%, or at least 55%, or at least 60% cellulose conversion, meaning that at least the specified theoretical yield of glucose monomers is obtained. A substantial portion of xylo-oligomers present in liquid fraction can typically be hydrolysed to xylose monomers by action of xylanase and other enzymes that remain active within the hydrolysate mixture. In some embodiments post-hydrolysis is conducted for at least 6 hours, or for a time between and 50 hours, or for at least 24 hours. In some embodiments, at least 60%, or at least 65%, or at least 70%, or at least 75%, or at least 80%, or at least 85%, or at least 90% by 25 mass of xylo-oligomers present in the liquid fraction are hydrolysed to xylose monomers during post-hydrolysis by action of xylanase and other enzymes that remain active within the hydrolysate mixture. In some embodiments, the liquid fraction is mixed with hydrolysate directly, without further addition of chemical additives. In some embodiments, some components of liquid fraction such as acetic acid, furfural or phenols may be removed from liquid fraction prior to mixing with hydrolysate.

In some embodiments, enzymatic hydrolysis of the solid fraction and/or post-hydrolysis of the liquid fraction may be conducted as a simultaneous saccharification and fermentation (SSF) process. As is well known in the art, when SSF can be conducted at the same temperature as that which is optimal for enzymatic hydrolysis, enzyme consumption can be minimized because a fermentive organism introduced during the course of enzymatic hydrolysis consumes glucose and xylose monomers and thereby reduces product inhibition of enzyme catalyzed reactions. In some embodiments, post-hydrolysis is only conducted after the fiber fraction has been hydrolysed, without addition of fermentive organism, to at least 60% cellulose conversion.

Where biomass feedstocks such as typical strains of wheat straw, sugar cane bagasse, sweet sorghum bagasse, corn stover or empty fruit bunches are pretreated at 35% or greater DM by single-stage autohydrolysis to xylan number 10% or greater, where solid fraction of the pretreated biomass is obtained having at least 40% DM or having at least 50% removal of dissolved solids, where solid fraction is subsequently subject to enzymatic hydrolysis at DM between 15 and 27% using a commercially available cellulase preparation optimized for lignocellulosic biomass conversion, where enzymatic hydrolysis is conducted for at least 48 hours, where liquid fraction is added to the solid fraction hydrolysate after at least 50% glucose conversion has been obtained, and where the added liquid fraction is subject to post-hydrolysis for a period of at least 6 hours, it is typically possible to achieve C5 monomer concentrations in the combined C5/C6 hydrolysate that correspond to C5 monomer yields of 60% or greater of the theoretical maximal xylose yield.

In some embodiments, the combined C5/C6 hydrolysate can be directly fermented to ethanol using one or more modified yeast strains.

Figure 9:
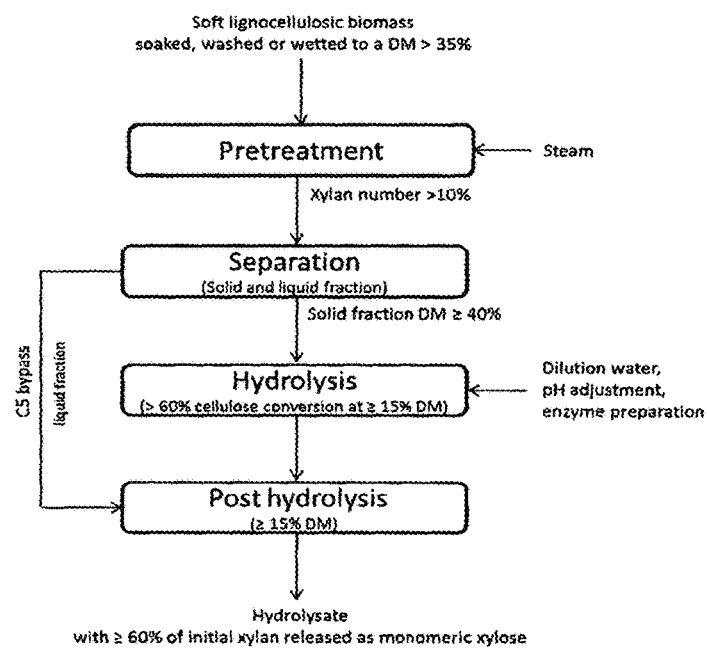
FIG. 9 shows a process scheme for one embodiment, wherein the abbreviation DM refers to dry matter.

FIG. 9 shows a process scheme for one embodiment. As shown, soft lignocellulosic biomass is soaked, washed or wetted to DM 35% or greater. The biomass is pretreated at pH within the range of 3.5 to 9.0 using pressurized steam in single-stage autohydrolysis to a severity characterized by xylan number 10% or greater. The pretreated biomass is subject to solid/liquid separation producing a liquid fraction and a solid fraction having DM content 40% or greater. The solid fraction is adjusted to an appropriate DM content then subject to enzymatic hydrolysis at DM content 15% or greater to a degree of cellulose conversion 60% or greater. The separated liquid fraction is subsequently mixed with the hydrolysed solid fraction and subject to post-hydrolysis, whereby a substantial quantity of xylo-oligomers present in the liquid fraction are hydrolysed to monomeric xylose. After the end of hydrolysis and post-hydrolysis as described, the C5 monomer yield is typically at least 60% while the cellulose conversion is similarly at least 60%.

EXAMPLES

Example 1. "Xylan Number" Characterization of Solid Fraction as a Measure of Pretreatment Severity Wheat straw (WS), corn stover (CS), Sweet sugarcane bagasse (SCB) and Empty Fruit Bunches (EFB) were soaked with 0-10 g acetic acid/kg dry matter biomass, pH>4.0, prior to pretreatment at 35-50% dry matter about 60 kg DM/h biomass was pretreated at temperatures from 170-200° C. with a residence time of 12-18 minutes. The biomass was loaded into the reactor using a sluice system and the pretreated material unloaded using a sluice system. The pressure within the pressurized pretreatment reactor corresponded to the pressure of saturated steam at the temperature used. The pretreated biomass was subject to solid/liquid separation using a screw press, producing a liquid fraction and a solid fraction having about 30% dry matter. The solid fraction was washed with about 3 kg water/kg dry biomass and pressed to about 30% dry matter again. Details concerning the pretreatment reactor and process are further described in Petersen et al. (2009).

Raw feedstocks were analysed for carbohydrates according to the methods described in Sluiter el al. (2005) and Sluiter et al. (2008) using a Dionex Ultimate 3000 HPLC system equipped with a Rezex Monossacharide H+ column from Phenomenex. Samples of liquid fraction and solid fraction were collected after three hours of continuous pretreatment and samples were collected three times over three hours to ensure that a sample was obtained from steady state pretreatment. The solid fractions were analysed for carbohydrates according to the methods described in Sluiter et al. (2008) with an Ultimate 3000 HPLC system from Dionex equipped with a Rezex Monossacharide H+ Monosaccharide column. The liquid fractions were analysed for carbohydrates and degradation products according to the methods described in Sluiter et al. (2006) with an Ultimate 3000 HPLC system from Dionex equipped with a Rezex Monossacharide H+ Monosaccharide column. Degradation products in the solid fraction were analysed by suspension of the solid fraction in water with 5 mM sulphuric acid in a ratio of 1:4 and afterward analysed according to the methods described in Sluiter et al. (2006) with an Ultimate 3000 HPLC system from Dionex equipped with a Rezex Monossacharide H+ column. The dry matter content and the amount of suspended solids was analysed according to the methods described in Weiss et al. (2009). Mass balances were set up as described in Petersen et al. (2009) and cellulose and hemicellulose recoveries were determined. The amount of sugars which were degraded to 5-HMF or furfural and the amount of acetate released from hemicelleulose during pretreatment per kg of biomass dry matter was quantified as well, although loss of furfural due to flashing is not accounted for.

The severity of a pretreatment process is commonly described by a severity factor, first developed by Overend et al. (1987). The severity factor is typically expressed as a log value such that $\log(R_0)=t*\mathrm{eksp}((T-T\mathrm{ref})/14.75)$, where $R_0$ is the severity factor, t is the residence time in minutes, T is the temperature and $T_{ref}$ is the reference temperature, typically 100° C. The severity factor is based on kinetics of hemicellulose solubilisation as described by Belkecemi et al. (1991), Jacobsen and Wyman (2000) or Lloyd et al. (2003). The severity of a pretreatment is thus related to residual hemicellulose content remaining in the solid fraction after pretreatment.

Solid fractions prepared and washed as described were analysed for C5 content according to the methods described by Sluiter et al. (2008) with a Dionex Ultimate 3000 HPLC system equipped with a Rezex Monossacharide H+ column from Phenomenex. The xylan content in the solid fraction produced and washed as described above is linearly depended upon the severity factor for soft lignocellulosic biomasses such as for example wheat straw, corn stover of EFB when pretreating by hydrothermal autohydrolysis. The definition of severity as the xylan content in a solid fraction prepared and washed as described above is transferable between pretreatment setups. Xylan number is the measured xylan content in the washed solid fractions, which includes some contribution from soluble material. The dependence of xylan number on pretreatment severity $\log(R_o)$ is shown in FIG. 1 for wheat straw, corn stover, sugarcane bagasse and empty fruit bunches from palm oil processing.

As shown, there exists a clear, negative linear correlation between xylan number and pretreatment severity for each of the tested biomass feedstocks pretreated by single-stage autohydrolysis.

Example 2. C5 Recovery as a Function of Pretreatment Severity

Figure 2:
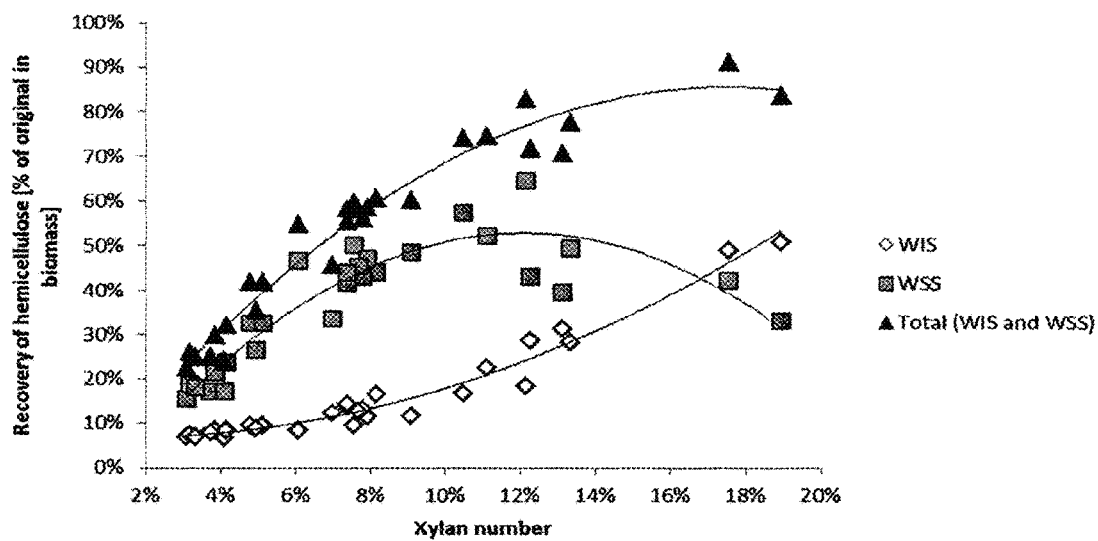
FIG. 2 shows C5 recovery in soluble and insoluble form as a function of xylan number for soft lignocellulosic biomass feedstocks subject to autohydrolysis pretreatment. Specifically.
Figure 3:
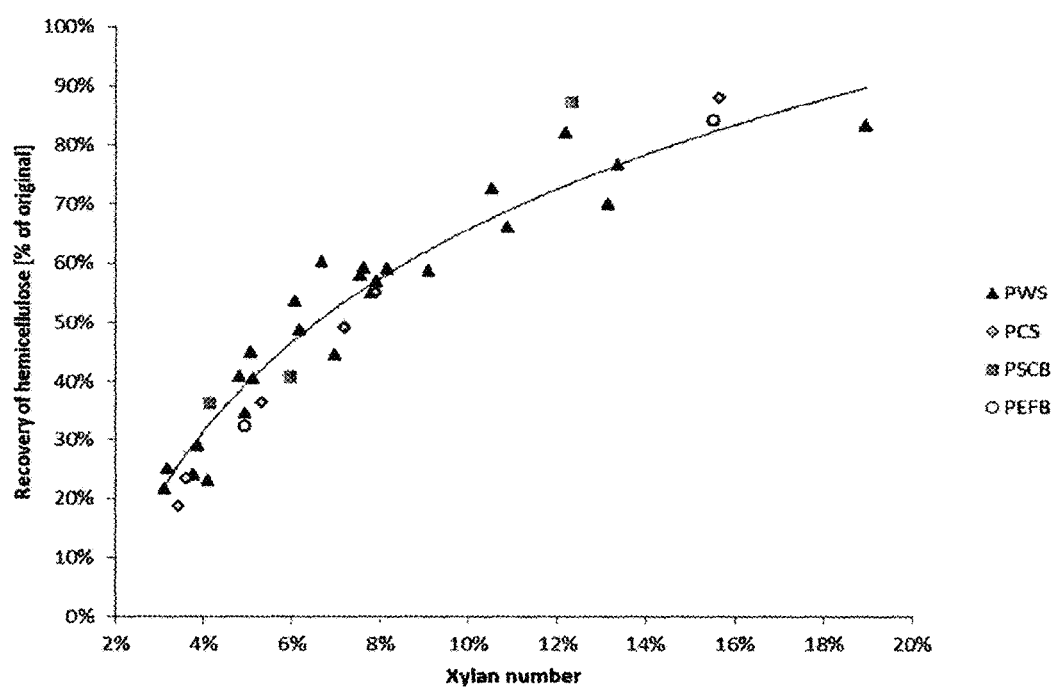
FIG. 3 shows total C5 recovery as a function of xylan number for soft lignocellulosic biomass feedstocks subject to autohydrolysis pretreatment. Specifically

Biomass feedstocks were pretreated and samples characterized as described in example 1. FIG. 2 shows the C5 recoveries (xylose+arabinose) as a function of xylan number for experiments where wheat straw was pretreated by autohydrolysis. C5 recoveries are shown as water insoluble solids (WIS), water soluble solids (WSS) and total recovery. As shown, C5 recovery as both water insoluble and water soluble solids increases as xylan number increases. As xylan number increases over 10%, C5 recovery as water soluble solids diminishes while C5 recovery as water insoluble solids continues to increase Typical strains of wheat straw tested contained about 27% hemicellulose on dry matter basis prior to pretreatment. FIG. 3 shows total C5 recovery after pretreatment as a function of xylan number for wheat straw, corn stover, sugarcane bagasse and EFB pretreated by autohydrolysis. Typical strains of corn stover, sweet sugarcane bagasse and EFB tested contained about 25%, 19% and 23% respectively of C5 content on dry matter basis prior to pretreatment. As shown, for all feedstocks, total C5 recovery after pretreatment is dependent upon pretreatment severity as defined by xylan number. As shown, where 90% of C5 content recovered after pretreatment can be fully hydrolysed to C5 monomer, a 60% final C5 monomer yield after enzymatic hydrolysis can be expected where pretreatment severity is characterized by producing a xylan number of 10% or higher.

Figure 4:
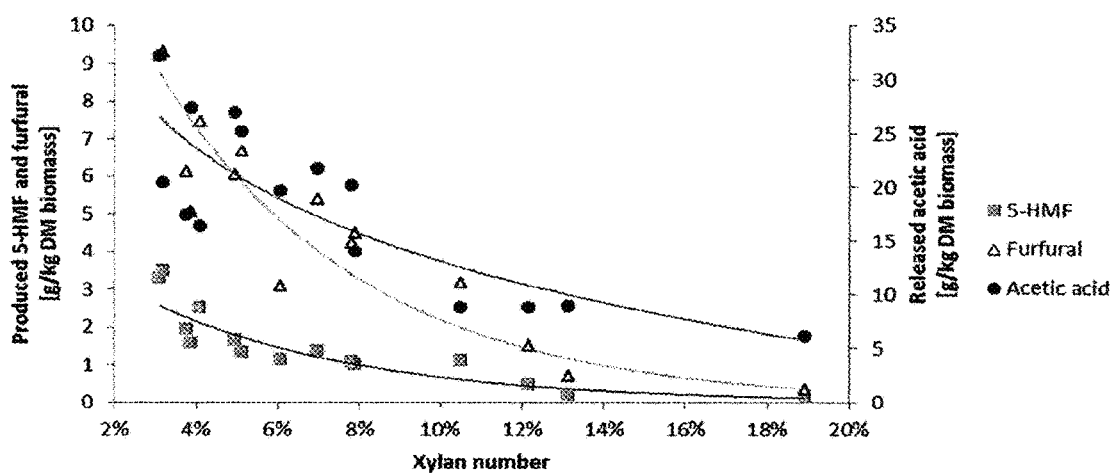
FIG. 4 shows production of acetic acid, furfural and 5-(hydroxymethyl)furfural (5-HMF) as a function of xylan number for soft lignocellulosic biomass feedstocks subject to autohydrolysis pretreatment.

Example 3. Production of Degradation Products that Inhibit Enzymes and Yeast Growth as a Function of Pretreatment Severity Biomass feedstocks were pretreated and samples characterized as described in example 1. FIG. 4 shows the dependence of acetic acid release and production of furfural and 5-hydroxy-methyl-fufural (5-HMF) as a function of xylan number for experiments where wheat straw was pretreated by single-stage autohydrolysis. As shown, production of these degradation products, which are well known to inhibit fermentive yeast and which in some cases also inhibit cellulase enzymes, exhibits an exponential increase at xylan numbers lower than 10%. At xylan number 10% and higher, the levels of furfural and acetic acid fall within ranges that permit fermentation of pretreated biomass without requirement of de-toxification steps. In the case of acetic acid, levels are further increased during enzymatic hydrolysis of biomass pretreated to xylan number 10% and higher, although typically to levels that are well tolerated by yeast modified to consume both C5 and C6 sugars.

Example 4. Inhibition of Cellulase Enzymes by Material Remaining in Solid Fraction as a Function of DM % of Solid Fraction Experiments were conducted in a 6-chamber free fall reactor working in principle as the 6-chamber reactor described and used in WO2006/056838. The 6-chamber hydrolysis reactor was designed in order to perform experiments with liquefaction and hydrolysis at solid concentrations above 20% DM. The reactor consists of a horizontally placed drum divided into 6 separate chambers each 24 cm wide and 50 cm in height. A horizontal rotating shaft mounted with three paddles in each chamber is used for mixing/agitation. A 1.1 kW motor is used as drive and the rotational speed is adjustable within the range of 2.5 and 16.5 rpm. The direction of rotation is programmed to shift every second minute between clock and anti-clock wise. A water-filled heating jacket on the outside enables control of the temperature up to 80° C.

The experiments used wheat straw, pretreated by single-stage autohydrolysis. The biomass was wetted to a DM of >35% and pretreated at pH>4.0 by steam to xylan number 10.5%. The pretreatment was conducted in the Inbicon pilot plant in Skærbæk, Denmark. The biomass was loaded into the pretreatment reactor using a sluice system and the pretreated biomass removed from the reactor using a sluice system. The pretreated biomass was, in some cases, subject to solid/liquid separation using a screw press, producing a liquid fraction and a solid fraction. The solid fraction had a DM content of about 30%, contained the majority of initial cellulose and lignin, part of the hemicellulose and a total of about 25% of the dissolved solids.

The chambers of the 6 chamber reactor were filled with either total pretreated biomass comprising all dissolved and undissolved solids or pressed solid fraction comprising about 25% of total dissolved solids. Dry matter content was adjusted to 19% DM. The pretreated biomass was then hydrolyzed at 50° C. and pH 5.0 to 5.3 using 0.08 ml CTec2™ from Novozymes/g glucan or 0.2-0.3 ml Accellerase TRIO™ from Dupont, Genencor/g glucan. These dose levels of these commercially available cellulase preparations optimized for lignocellulosic biomass conversion were well within the range suggested by the manufacturers. Enzymatic hydrolysis experiments were conducted for 96 hours at a mixing speed of 6 rpm.

Figure 5:
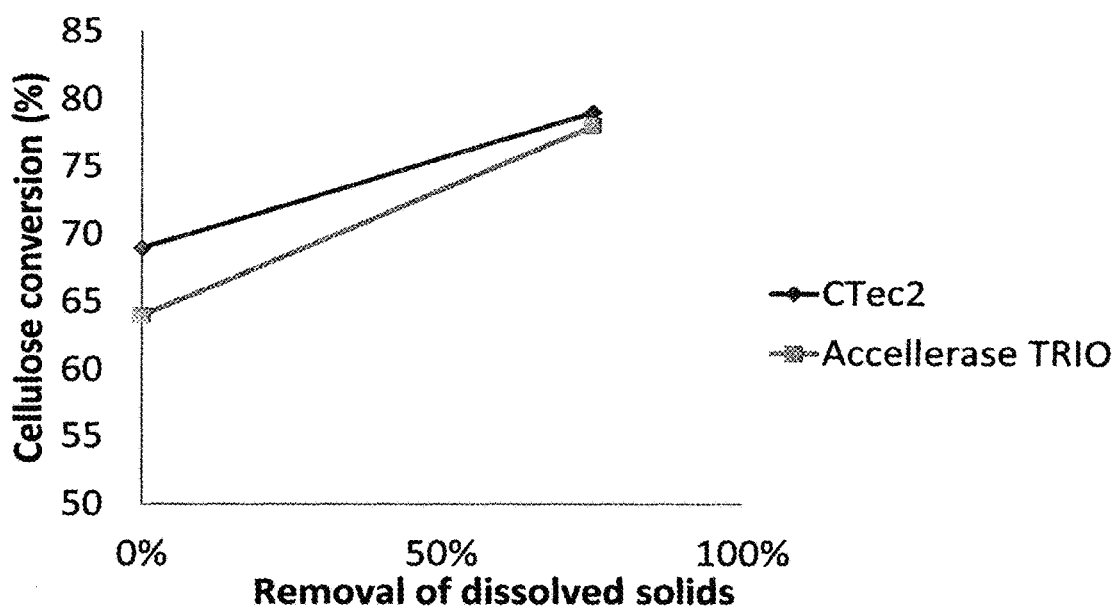
FIG. 5 shows the effect of removal of dissolved solids on cellulose conversion for soft lignocellulosic biomass feedstocks subject to very low severity autohydrolysis pretreatment.

FIG. 5 shows cellulose conversion after enzymatic hydrolysis under these conditions as a function of % dissolved solids removed prior to enzymatic hydrolysis. As shown, removal of 75% dissolved solids at these enzyme dose levels improves cellulose conversion by 10-20% in absolute terms. Thus, it is advantageous to press solid fraction to DM content at least 40% or to otherwise reduce dissolved solids content by at least 50% prior to enzymatic hydrolysis, since this will provide improved enzyme performance.

Example 5. Sugar Content and Hydrolysis of Liquid Fraction From Biomass Pretreated to Xylan Number >10%

Wheat straw, corn stover, and sugar cane bagasse were pretreated to xylan number 11.5% (WS), 12.3% (SCB) and 15.5% (CS) and subject to solid/liquid separation to produce a liquid fraction and a solid fraction, as described in example 5. The liquid fractions were analysed for carbohydrates and degradation products according to the methods described in (Sluiter, Hames et al. 2005) using a Dionex Ultimate 3000 HPLC system equipped with a Rezex Monosaccharide column. Table 2 shows the sugar content of liquid fractions expressed as a percent of DM content broken down into categories of oligomeric and monomeric glucose/glucan, xylose/xylan and arabinose/arabinan. As shown, while some glucose content is present in both monomeric and oligomeric form, the bulk of the sugar content is oligomeric xylan. The predominance of xylan oligomers in liquid fraction obtained using autohydrolysis is in noted contrast with the liquid fraction obtained using dilute acid pretreatment. In biomass pretreated by dilute acid hydrothermal pretreatment, the liquid fraction is typically hydrolysed to monomeric constituents by actions of the acid catalyst.

TABLE 2

Sugar content of liquid fractions in biomass pretreated to xylan number > 10%.

|     | Oligomeric glucan | Monomeric glucose | Oligomeric xylan | Monomeric xylose | Oligomeric arabinan | Monomeric arabinose | Other DM |
| --- | --- | --- | --- | --- | --- | --- | --- |
| WS  | 5.5% | 2.1% | 40.4% | 8.6% | 1.1% | 4.8% | 37% |
| SCB | 8.2% | 3.1% | 39.1% | 8.7% | 0.7% | 3.1% | 37% |
| SC  | 6.2% | 1.9% | 37.0% | 5.3% | 2.8% | 3.9% | 43% |

Figure 6:
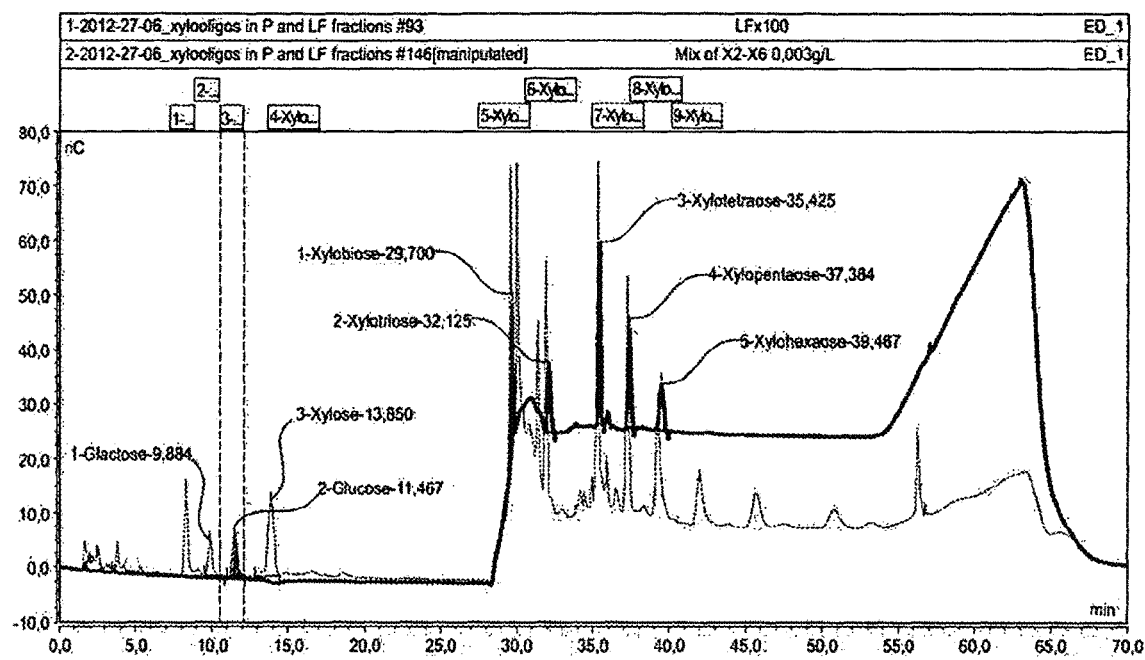
FIG. 6 shows high performance liquid chromatography (HPLC) characterization of liquid fraction from soft lignocellulosic biomass feedstocks subject to very low severity autohydrolysis pretreatment. Specifically.

The liquid fraction from pretreated wheat straw was further characterized by HPLC analysis using a Thermo Scientific Dionex CarboPac™ PA200 column using a modular Dionex ICS-5000 chromatographic system. The analytes were separated using NaOH/NaOAc-gradient conditions and measured by integrated and pulsed amperometric detection (IPAD) using a gold electrode. FIG. 6 shows an HPLC chromatogram in which the elution profile of xylobiose ($X_2$), xylotriose ($X_3$), xylotetraose ($X_4$), xylopentaose ($X_5$), and xylohexaose ($X_6$) standards is super-imposed as the upper trace over the lower trace, which depicts the elution profile of liquid fraction. As shown, liquid fraction of the autohydrolysed biomass contains a mixture comprising a small amount of xylose monomer and comparatively larger amounts of xylobiose ($X_2$), xylotriose ($X_3$), xylotetraose ($X_4$), xylopentaose ($X_5$), and xylohexaose ($X_6$), along with other materials.

Example 6. Enzymatic Hydrolysis of Solid Fraction and Addition of Liquid Fraction After the Fibre Hydrolysis From Biomass Pretreated to Xylan Number >10% and Pressed to >40% DM Followed by Post Hydrolysis Experiments were conducted in a 6-chamber free fall reactor as described in example 4.

The experiments used wheat straw, corn stover, or sugar cane bagasse pretreated by single-stage autohydrolysis to xylan numbers ranging from 11.5 to 15.6%. The biomass was cut and wetted to a DM of >35% and pretreated by steam at 170-190° C. for 12 min. The pretreatment was conducted in the Inbicon pilot plant in Skærbæk, Denmark. The pretreated biomass was subject to solid/liquid separation using a screw press to produce a solid fraction having >40% DM.

The chambers of the 6 chamber reactor were filled with about 10 kg pressed pretreated biomass and adjusted by water addition to 19-22% DM. The pretreated biomass was hydrolyzed at 50° C. and pH 5.0 to 5.3 using ACCELLERASE TRIO™ from GENENCOR-DuPONT. The mixing speed was 6 rpm. The hydrolysis experiments were run for 96 hours and afterwards the liquid fraction pressed from the solid fraction after pretreatment was added and the post hydrolysis was run for 48 hours at 50° C. and pH 5.0 to 5.3.

HPLC samples were taken daily to follow the conversion of cellulose and hemicellulose and analysed for glucose, xylose and arabinose using a Dionex Ultimate 3000 HPLC system equipped with a Rezex Monosaccharide column with quantification through use of external standard.

Figure 7:
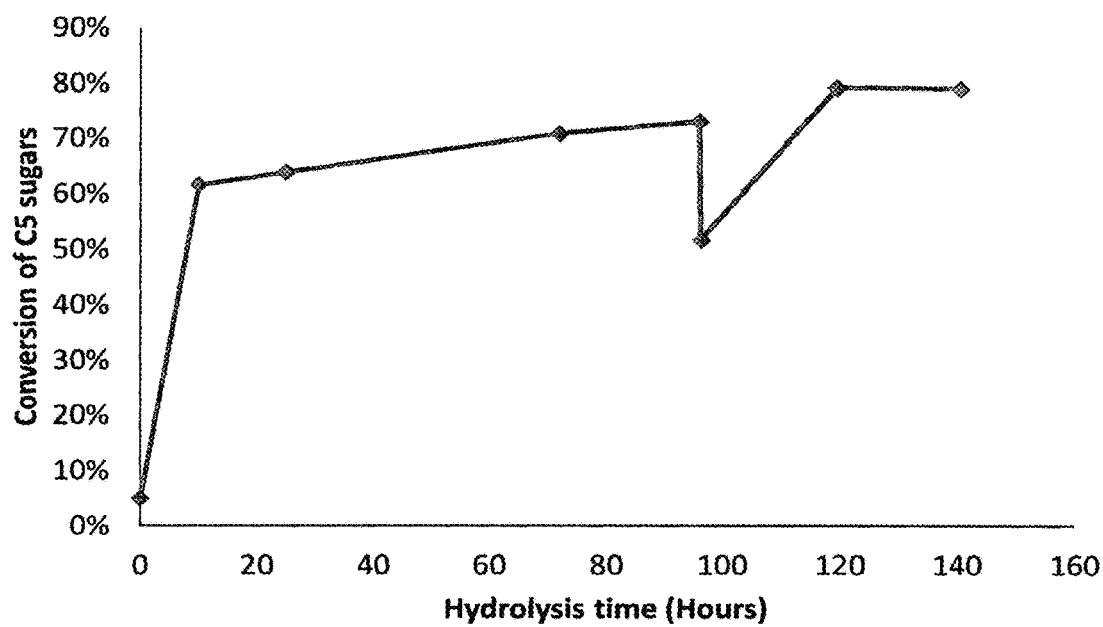
FIG. 7 shows C5 sugar recovery as a function of time where solid fraction is subject to enzymatic hydrolysis followed by introduction of liquid fraction for post-hydrolysis. Specifically.

FIG. 7 shows hydrolysis data for conversion of hemicellulose with addition of liquid fraction after 96 hours hydrolysis of solid fraction using sugar cane bagasse pretreated to xylan number 12.3% and hydrolysed using 0.3 ml Accellerase Trio™ (Genencor) per g glucan. Shown is a typical hydrolysis profile. C5 monomer recovery is expressed as a percent of theoretical yield from the material present in the hydrolysis reaction. Most of the hemicellulose within the solid fraction has been converted to monomeric sugars within the first 24 hours in hydrolysis of the solid fraction. Addition of liquid fraction after 96 hours increases the theoretical potential yield, which explains the drop in C5 conversion observed just after liquid fraction is added. Within the first 24 hours most of the C5 from liquid fraction is converted to monomers. Comparing the C5 conversion just before liquid fraction is added with the end point of the hydrolysis, it is possible to calculate the C5 conversion in the liquid fraction as 90% when using sugar cane bagasse under these conditions.

Table 3 shows hydrolysis data for different biomasses pretreated under different circumstances and hydrolysed using different dose levels of a commercially available cellulase preparation optimized for lignocellulosic biomass conversion, Accellerase Trio™ (Genencor). All enzyme dose levels used were within the range suggested by the manufacturer. As shown, using single-stage autohydrolysis and enzymatic hydrolysis with C5 bypass and post-hydrolysis, C5 monomer yields of 60% or greater can be achieved using manufacturers' recommended doses of commercially available cellulase preparations optimized for lignocellulosic biomass conversion while still achieving cellulose conversion of 60% or greater.

TABLE 3

Hydrolysis yields using very low severity single-stage autohydrolysis with C5 bypass and post-hydrolysis.

|     | WS | SCB | SCB | CS | CS | EFB |
| --- | --- | --- | --- | --- | --- | --- |
| Dry matter after soaking [wt %] | 40% | 39% | 39% | 40% | 40% | 39% |
| Residence time [min] | 12.0 | 12.0 | 12.0 | 12.0 | 12.0 | 12.0 |
| Temperature [° C.] | 183.0 | 182.7 | 182.7 | 174.5 | 174.5 | 185.2 |
| Pretreatment severity [logRo] | 3.52 | 3.51 | 3.51 | 3.27 | 3.27 | 3.58 |
| C5 recovery from pretreatment [%] | 74% | 87% | 87% | 88% | 88% | 84% |
| Xylan number | 11.5% | 12.3% | 12.3% | 15.6% | 15.6% | 15.5% |
| Enzyme dosage [mL Ac. TRIO/g glucan] | 0.2 | 0.3 | 0.3 | 0.3 | 0.2 | 0.4 |
| % TS in fiber hydrolysis | 22% | 22% | 22% | 19% | 22% | 22% |

TABLE 3-continued

Hydrolysis yields using very low severity single-stage autohydrolysis with C5 bypass and post-hydrolysis.

|  | WS | SCB | SCB | CS | CS | EFB |
|---|---|---|---|---|---|---|
| Cellulose conversion after hydrolysis (96 h) | 78% | 64% | 66% | 68% | 58% | 69% |
| Hemicellulose conversion (C5 recovery) after hydrolysis (96 h) | 80% | 73% | 73% | 61% | 61% | 75% |
| % TS in second hydrolysis | 18% | 17% | 17% | 16% | 18% | 18 |
| Cellulose conversion after post hydrolysis (144 h) | 78% | 65% | 67% | 67% | 61% | 72% |
| Hemicellulose conversion (C5 recovery) after post hydrolysis (144 h) | 90% | 79% | 78% | 71% | 68% | 83% |
| Overall cellulose conversion | 78% | 65% | 67% | 67% | 61% | 72% |
| Overall C5 monomer yield | 67% | 69% | 68% | 63% | 60% | 70% |

Figure 8:
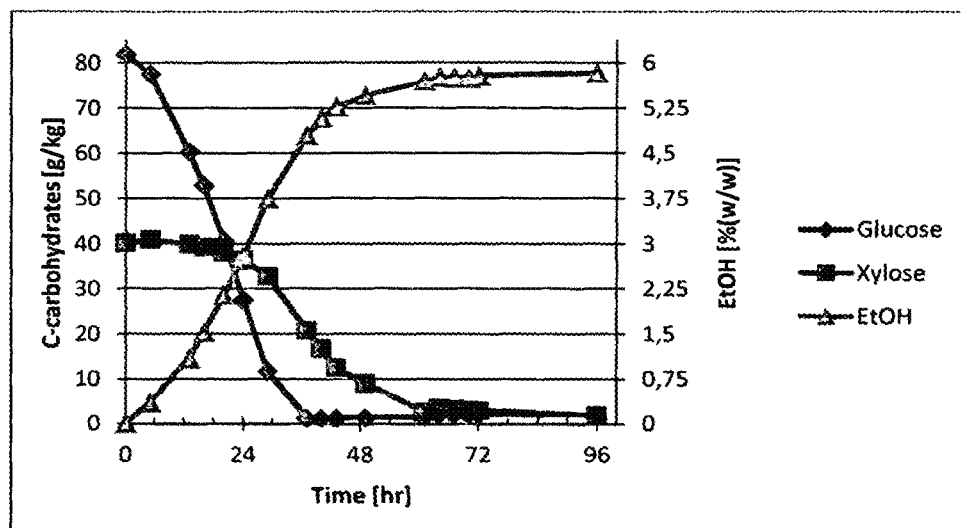
FIG. 8 shows fermentation profile of ethanol fermentation by a modified yeast strain using wheat straw that was pretreated by very low severity autohydrolysis, enzymatically hydrolysed and used as combined liquid and solid fraction without de-toxification to remove fermentation inhibitors. Specifically.

Example 7. Co-Fermentation to Ethanol of C5 and C6 Sugars in Combined Hydrolysate by Modified Yeast As an example on the use of a hydrolysate produced from soft lignocellulosic biomass (in this case wheat straw) prepared by single-stage autohydrolysis pretreatment to a xylan number >10%, FIG. 8 shows data for a fermentation performed without detoxification or any other process steps before fermentation with GMO yeast able to convert both C5 and C6 sugars (strain V1 from TERRANOL™). The hydrolysate was adjusted to pH 5.5 with KOH pellets before fermentation and supplemented with 3 g/L urea. The fermentation was conducted as a batch fermentation. The initial cell concentration in the reactor was 0.75 g dw/L. The fermentations were controlled at pH 5.5 using automatic addition of 10% NH3.

The temperature was kept at 30° C. and the stirring rate was 300 rpm. As shown, glucose and xylose are readily consumed and ethanol readily produced, notwithstanding the presence of acetic acid, furfural and other compounds that would typically prove inhibitory at higher levels of pretreatment severity.

Example 8. Experimental Determination of Activity Levels in Commercial Cellulase Preparations Commercial preparations of ACCELLERASE TRIO™ from GENENCOR™ and CELLIC CTEC2™ and CELLIC CTEC3™ from NOVOZYMES™ were diluted so that protein concentrations were roughly equivalent in sample preparations tested. Equivalent volumes of diluted enzyme preparations were added and assay determinations made in duplicate or triplicate.

Assay of CBHI (exocellulase) activity was conducted in 50 mM NaOAC buffer at pH 5, 25° C., for 25 minutes. Activity was determined in triplicate by following continuous rate of 4-Methylumbelliferon release (Abs: 347 nm) from the model substrate 4-methylumbelliferyl-β-cellobioside. Activity unit was 1 umole MeUmb equivalent/minute. Protein concentrations were 0.16, 0.14, 0.17 mg/ml respectively for CTEC3, ACTrio, and CTEC2 assays. Substrate concentration was 0.5 mg/ml.

Assay of Endo-1,4-β-glucanase activity was conducted in 50 mM NaOAC buffer, pH 5; 50° C., for 60 minutes. Activity was determined in triplicate by following absorbance change associated with generation of reducing ends from the model substrate Avicel PH-101. Activity unit was 1 μmole glucose equivalent/min. Protein concentrations were 0.80, 0.67, 0.79 mg/ml respectively for CTEC3, ACTrio, and CTEC2 assays. Substrate concentration was 80 mg/ml.

Assay of β-glucosidase activity was conducted in 50 mM NaOAC buffer, pH 5; 50° C., for 20 minutes. Activity was determined in triplicate by following absorbance change associated with release of glucose from model substrate cellobiose. Activity unit was 2 μmole glucose/min. Protein concentrations were 0.1, 0.12, 0.12 mg/ml respectively for CTEC3, ACTrio, and CTEC2 assays. Substrate concentration was 1.7 mg/ml.

Assay of Endo-1,4-β-xylanase activity was conducted in 50 mM NaOAC buffer, pH 5; 50° C., for 60 minutes. Activity was determined in triplicate by following absorbance change associated with generation of reducing ends from the model substrate water extractable arabinoxylan. Activity unit was 1 μmole glucose equivalent/min. Protein concentrations were 1.12, 0.97, 1.12 mg/ml respectively for CTEC3, ACTrio, and CTEC2 assays. Substrate concentration was 10 mg/ml.

Assay of β-xylosidase activity was conducted in 50 mM NaOAC buffer, pH 5; 50° C., for 60 minutes. Activity was determined in duplicate by following release of xylose associated with hydrolysis of the model substrate water extractable arabionxylan. Activity unit was 1 μmole xylose/min. Protein concentrations were 1.12, 0.97, 1.12 mg/ml respectively for CTEC3, ACTrio, and CTEC2 assays. Substrate concentration was 10 mg/ml.

Assay of β-L-arabinofuranosidase activity was conducted in 50 mM NaOAC buffer, pH 5; 50° C., for 60 minutes. Activity was determined in triplicate by following release of arabinoase associated with hydrolysis of the model substrate water extractable arabinoxylan. Activity unit was 1 μmole arabinose/min. Protein concentrations were 1.12, 0.97, 1.12 mg/ml respectively for CTEC3, ACTrio, and CTEC2 assays. Substrate concentration was 10 mg/ml.

Assay of amyloglucosidase (AMG) activity was conducted in 50 mM NaOAC buffer, pH 5; 50° C., for 80 minutes. Activity was determined in triplicate by following absorbance change associated with glucose release from the model substrate soluble corn starch. Activity unit was 1 μmole glucose/min. Protein concentrations were 1.12, 0.97, 1.12 mg/ml respectively for CTEC3, ACTrio, and CTEC2 assays. Substrate concentration was 10 mg/ml.

Assay of α-amylase activity was conducted in 50 mM NaOAC buffer, pH 5; 50° C., for 60 minutes. Activity was determined in triplicate by following absorbance change associated with generation of reducing ends from the model substrate soluble corn starch. Activity unit was 1 μmole glucose equivalent/min. Protein concentrations were 1.12, 0.97, 1.12 mg/ml respectively for CTEC3, ACTrio, and CTEC2 assays. Substrate concentration was 10 mg/ml.

Assay of acetyl xylan esterase activity was conducted in 100 mM Succinate buffer, pH 5; 25° C., for 25 minutes.

Activity was determined in triplicate by following continuous rate of 4-Nitrophenyl release (Abs: 410 nm) from the model substrate 4 4-Nitrophenyl acetate. Activity unit was 1 µmole pNP equivalent/min. Protein concentrations were 0.48, 0.42, 0.51 mg/ml respectively for CTEC3, ACTrio, and CTEC2 assays. Substrate concentration was 10 mg/ml.

Results of the activity determinations are shown in Table 1.

The embodiments and examples are descriptive only and not intended to limit the scope of the claims.

REFERENCES

Agbor, V., et al. "Biomass pretreatment: Fundamentals toward application", Biotechnology Advances (2011) 29:675

Alvira, P., et al. "Pretreatment technologies for an efficient bioethanol production process based on enzymatic hydrolysis: A review", Bioresource Technology (2010) 101:4851

Baboukani, B., et al. "Optimisation of dilute-acid pretreatment conditions for enhancement sugar recovery and enzymatic hydrolysis of wheat straw", Biosystems Engineering III (2012) 166

Banerjee, G., Car, S., Scott-Craig, J., Borrusch, M., and Walton, D., "Rapid optimisation of enzyme mixtures for deconstruction of diverse pretreatment/biomass feedstock combinations," Biotechnology for Biofuels (2010), 3:22.

Belkacemi, K., Abatzoglou, N., Overend, R. P., Chornet, E., "Phenomenological Kinetics of Complex Systems: Mechanistic Considerations in the Solubilization of Hemicelluloses following Aqueous/Steam Treatments." *Ind. Eng. Chem. res.*, (1991) 30, 2416-2425.

Bettiga, M., et al. "Arabinose and xylose fermentation by recombinant Saccharomyces cerevisiae expressing a fungal pentose utilization pathway", Microbial Cell Factories (2009) 8:40

Billard, H., Faraj., A., Ferreira, N., Menir, S., and Heiss-Blanquet, S., "Optimisation of a synthetic mixture composed of major *Trichoderma ressei* enzymes for the hydrolysis of steam-exploded wheat straw," Biotechnology for Biofuels (2012), 5:9.

Chen, Y., et al. "Xylose and cellulose fractionation from corncob with three different strategies and separate fermentation of them to bioethanol", Bioresource Technology (2010) 101:6994

Chung, Y., et al. "Enzymatic Saccharification and Fermentation of Xylose-Optimized Dilute Acid-Treated Lignocellulosics", Applied Biochemistry and Biotechnology (2005) 121-124:947

Diaz, M., et al. "Hydrothermal pretreatment of rapeseed straw", Bioresource Technology (2010) 101:2428

Divne, C., et al., "The 3-dimensional crystal-structure of the catalytic core of cellobiohydrolase-I from *Trichoderma reesei*," Science (1994), 265:524.

Dogaris, I., et al. "Hydrothermal processing and enzymatic hydrolysis of sorghum bagasse for fermentable carbohydrates production", Bioresource Technology (2009) 100:6543

Dumon, C., et al. "Progress and future prospects for pentose-specific biocatalysts in biorefining", Process Biochemistry (2012) 47:346

Farrell, E et al., "Ethanol can contribute to energy and environmental goals," Science (2006), 311:506.

Ghosh, A., et al. "Genome-Scale Consequences of Cofactor Balancing in Engineered Pentose Utilization Pathways in Saccharomyces cerevisiae", PLoS ONE (2011) 6:11

Girio, F., et al., "Hemicelluloses for fuel ethanol: A review," Bioresource Technology (2010), 101:4775

Hu, C., et al. "Simultaneous utilization of glucose and xylose for lipid production by Trichosporon cutaneum", Biotechnology and Biofuels (2011) 4:25

Humbird, D., et al. "Process Design and Economic for Biochemical Conversion of Lignocellulosic Biomass to Ethanol: Dilute-Acid Pretreatment and Enzymatic Hydrolysis of Corn Stover" Technical Report NREL/TP-5100-47764 May 2011

Humbird, D., et al., "Economic impact of Total Solids Loading on Enzymatic Hydrolysis of Dilute Acid Pretreated Corn Stover," Biotechnology Progress (2010) 26:1245

Jacobsen, S., et al. "Xylose Monomer and Oligomer Yields for Uncatalyzed Hydrolysis of Sugarcane Bagasse Hemicellulose at Varying Solids Concentration", Ind. Eng. Chem. Res. (2002) 41:1454

Jacobsen, S. E., Wyman, C. E., Cellulose and Hemicellulose Hydrolysis Models for Application to Current and Novel Pretreatment Processes. *Applied Biochemistry and Biotechnology* (2000), 84-86, 81-96.

Jeong, T., et al. "Optimizing Dilute-Acid Pretreatment of Rapeseed Straw for Extraction of Hemicellulose", Appl Biochem Biotechnol (2010) 161:22

Jin, M., et al. "Two-step SSCF to convert AFEX-treated switchgrass to ethanol using commercial enzymes and Saccharomyces cerevisiae 424A(LNH-ST)", Bioresource Technology (2010) 101:8171

Jojima, T., et al. "Sugar transporters in efficient utilization of mixed sugar substrates: current knowledge and outlook", Applied Microbiology and Biotechnology (2010) 85:471

Kim, J., et al. "Two-stage pretreatment of rice straw using aqueous ammonia and dilute acid", Bioresource Technology (2011) 102:8992

Kim, K. et al. "Continuous Countercurrent Extraction of Hemicellulose from Pretreated Wood Residues", Applied Biochemistry and Biotechnology (2001) 91-93:253

Klinke, H., et al., "Inhibition of ethanol-producing yeast and bacteria by degradation products produced during pretreatment of biomass," Appl. Microbiol. Biotechnol. (2004) 66:10.

Knudsen, N., et al., "Possibilities and evaluation of straw pretreatment," 10th European biomass conference in Würzburg in 1998, Biomass for Energy and Industry, p. 224-228.

Kothari, U., and Lee, Y., "Inhibition effects of dilute acid pre-hydrolysate of corn stover on enzymatic hydrolysis of solka floc," Applied. Biochem. Biotechnol. (2011) 165:1391

Kristensen, J., Felby, C., and Jørgensen, H., "Determining yields in high solids enzymatic hydrolysis of biomass," Appl. Biochem. Biotechno. (2009), 156:557.

Kuhad, R., et al. "Bioethanol production from pentose sugars: Current status and future prospects", Renewable and Sustainable Energy Reviews (2011) 15:4950

Kurian, J., et al. "BIOCONVERSION OF HEMICELLULOSE HYDROLYSATE OF SWEET SORGHUM BAGASSE TO ETHANOL BY USING PICHIA STIPITIS NCIM 3497 AND DEBARYOMYCES HANSEN!! SP.", Bioresources (2010) 5:2404

Larsen, J., et al. "The IBUS Process—Lignocellulosic Bioethanol Close to a Commercial Reality", Chem. Eng. Technol. (2008) 5:765

Lee, J., et al. "Autohydrolysis pretreatment of Coastal Bermuda grass for increased enzyme hydrolysis", Bioresource Technology (2009) 100:6434

Lee, J., et al. "Recent developments of key technologies on cellulosic ethanol production", Journal of Scientific & Industrial Research (2008) 67:865

Lee, J. et al. "Review article Biological conversion of lignocellulosic biomass to ethanol", Journal of Biotechnology (1997) 56:1

Leith, H and Whittaker, R, *Primary productivity of the biosphere*. Springer, Berlin. 1975. P. 205-206.

Lloyd, T., and Wyman, C. "Application of a Depolymerization Model for Predicting Thermochemical Hydrolysis of Hemicellulose." *Applied Biochemistry and Biotechnology* (2003), 105-108, 53-67.

Lu, X., et al. "Optimization of H2SO4-catalyzed hydrothermal pretreatment of rapeseed straw for bioconversion to ethanol: Focusing on pretreatment at high solids content", Bioresource Technology (2009) 100:3048

Madhavan, A., et al. "Bioconversion of lignocellulose-derived sugars to ethanol by engineered Saccharomyces cerevisiae", Critical Reviews in Biotechnology (2012) 32:22

Martinez, D., et al., "Genome sequencing and analysis of the biomass-degrading fungus *Trichoderma reesei,*" Nature Biotechnology (2008), 26:553.

Matsushika, A., et al. "Ethanol production from xylose in engineered Saccharomyces cerevisiae strains: current state and perspectives", Applied Microbiology and Biotechnology (2009) 84:37

Mesa, L. et al. "Comparison of process configurations for ethanol production from two-step pretreated sugarcane bagasse", Chemical Engineering Journal (2011) 175:185

Monavari, S., et al. "The influence of solid/liquid separation techniques on the sugar yield in two-step dilute acid hydrolysis of softwood followed by enzymatic hydrolysis", Biotechnology for Biofuels (2009) 2:6

Nguema-Ona, E., Moore, J., Fagerstrom, A., Fangel, J., Willats, W., Hugo, A., and Vivier, M., "Profiling the main cell wall polysaccharides of tobacco leaves using high-throughput and fractionation techniques", Carbohydrate Polymers (2012), 88:939

Ohgren, K., et al. "EVect of hemicellulose and lignin removal on enzymatic hydrolysis of steam pretreated corn stover", Bioresource Technology (2007) 98:2503

Overend, R. P., Chornet, E., "Fractionation of lignocellulosics by steam aqueous pretreatments" *Philos. Trans. R. Soc. Lond. A* (1987), 321, 523-536.

Palmquist E, H Grage, NQ Meinander and B Hahn-Hagerdal "Main and interaction effects of acetic acid, furfural, and phydroxybenzoic acid on growth and ethanol productivity of yeasts." Biotechnol. Bioeng. (1999) 63: 46-55

Paptheofanous, M., et al. "TWO-STAGE ACID-CATALYZED FRACTIONATION OF LIGNOCELLULOSIC BIOMASS IN AQUEOUS ETHANOL SYSTEMS AT LOW TEMPERATURES", Bioresource Technology (1995) 54:305

Petersen, M., et al. "Optimization of hydrothermal pretreatment of wheat straw for production of bioethanol at low water consumption without addition of chemicals", Biomass and Bioenergy (2009) 33:834

Quing, Q., Yang, B., Wyman, C., "Xylo-oligomers are strong inhibitors of cellulose hydrolysis by enzymes," Bioresource Technology (2010) 101:9624

Quing, Q., and Wyman, E., "Hydrolysis of different chain length xylo-oligomers by cellulase and hemicellulase enzymes," Bioresource Technology (2011) 102:1359

Rosgaard, L., et al., "Evaluation of minimal *Trichoderma reesei* cellulase mixtures on differently pretreated barley straw substrates," Biotechnol. Prog. (2007), 23:1270

Rouvinen, J., et al., "3-dimensional structure of cellobiohydrolase-II from *Trichoderma reesei,*" Science (1990), 249:380

Saha, B., et al. "Hemicellulose bioconversion", Microbiol Biotechnol (2003) 30:279

Sanchez, R., et al. "Improved xylose and arabinose utilization by an industrial recombinant *Saccharomyces cerevisiae* strain using evolutionary engineering", Biotechnology for Biofuels (2010) 3:13

Shen, F., et al. "Evaluation of hemicellulose removal by xylanase and delignification on SHF and SSF for bioethanol production with steam-pretreated substrates", Bioresource Technology (2011) 102:8945

Singhania, R., et al., "Advancement and comparative profiles in the production technologies using solid-state and submerged fermentation for microbial cellulases," Enzyme and Microbial Technology (2010), 46:541

Sluiter, A., et al., "Determination of Extractives in Biomass," US National Renewable Energy Laboratory (NREL), Laboratory Analytical Procedure (LAP) with issue date Jul. 17, 2005, NREL/TP-510-42619, revised January 2008

Sluiter, A., et al., "Determination of Sugars, Byproducts, and Degradation Products in Liquid Fraction Process Samples," US National Renewable Energy Laboratory (NREL), Laboratory Analytical Procedure (LAP) with issue date Dec. 8, 2006, NREL/TP-510-42623, revised January 2008

Sluiter, A., et al., "Determination of Structural Carbohydrates and Lignin in Biomass," US National Renewable Energy Laboratory (NREL), Laboratory Analytical Procedure (LAP) with issue date Apr. 25, 2008, NREL/TP-510-42618, revised April 2008

Soderstrom, J., et al. "Two-step steam pretreatment of softwood by dilute H2SO4 impregnation for ethanol production", Biomass and Bioenergy (2003) 24:475

Soderstrom, J., et al. "Effect of Washing on Yield in One- and Two-Step Steam Pretreatment of Softwood for Production of Ethanol", Biotechnol. Prog. (2004) 20:744

Soderstrom, J., et al. "Separate versus Simultaneous Saccharification and Fermentation of Two-Step Steam Pretreated Softwood for Ethanol Production", Journal of Wood Chemistry and Technology (2005) 25:187

Taherzadeh, M., et al. "Pretreatment of Lignocellulosic Wastes to Improve Ethanol and Biogas Production: A Review" International Journal Molecular Science (2008) 9:1621

Thomsen, M., et al. "Preliminary Results on Optimization of Pilot Scale Pretreatment of Wheat Straw Used in Coproduction of Bioethanol and Electricity", Applied Biochemistry and Biotechnology (2006) 129-132:448

Vinzant, T., et al., "Fingerprinting *Trichoderma reesei* hydrolases in a commercial cellulase preparation," Applied Biochem. and Biotechnol. (2001), 91-93:99

Weiss, N. D., et al., "A simplified Method for the Measurement of Insoluble Solids in Pretreated Biomass Slurries." *Appl. Biochem. Biotechnol.* (2009), 975-987:162(4)

Won, K., et al. "Fractionation of barley straw with dilute sulfuric acid for improving hemicellulose recovery", Korean Journal Chemical Engineering (2012) 29:614

Ximenes, E., et al. "Inhibition of cellulases by phenols," Enzyme and Microbial. Tecnol. (2010) 46:170

Zaldivar J, A Martinez and LO Ingram "Effects of selected aldehydes on the growth and fermentation of ethanologenic *Escherichia* 25 coll." Biotechnol. Bioeng. (1999) 65. 24-33

Zhang, P., et al., "Outlook for cellulase improvement: Screening and selection strategies," Biotechnology Advances (2006), 24:452

The invention claimed is:

1. A method of processing lignocellulosic biomass comprising:
   Pretreating a soft lignocellulosic biomass feedstock at a pH between 3.5 and 9.0 in a single-stage pressurized hydrothermal pretreatment reactor to very low severity such that the pretreated biomass has a xylan number of 10% or higher, wherein exogenous cellulase enzymes are not added during the pretreatment, and the pretreating does not comprise adding sulphuric acid to the feedstock;
   Separating the pretreated biomass into a solid fraction and a liquid fraction;
   Hydrolysing the solid fraction using enzymatic hydrolysis catalysed by an enzyme mixture comprising endoglucanase, exoglucanase, B-glucosidase, endoxylanase, xylosidase, and acetyl xylan esterase activities, wherein the enzyme mixture is not added to the liquid fraction; and
   Subsequently mixing the separated liquid fraction and the hydrolysed solid fraction;
   whereby xylo-oligomers in the liquid fraction are degraded to xylose monomers by action of enzyme activities remaining within the hydrolysed solid fraction.

2. The method of claim 1, wherein the feedstock is wheat straw, corn stover, sugar cane bagasse, sweet sorghum bagasse, or empty fruit bunches.

3. The method of claim 1, wherein the feedstock is washed and/or leached prior to pressurized pretreatment.

4. The method of claim 1, wherein the feedstock is soaked in an acetic acid containing liquid from a subsequent step of the pretreatment prior to pressurized pretreatment.

5. The method of claim 1, wherein the feedstock is subject to pressurized pretreatment at a dry matter content of at least 35%.

6. The method of claim 1, wherein pressurized pretreatment is conducted at a pressure of 10 bar or lower.

7. The method of claim 1, wherein the feedstock is removed from the pressurized pretreatment reactor using a hydrocyclone system or a sluice-type system.

8. The method of claim 1, wherein the feedstock is pretreated to a severity such that the biomass produced has a xylan number of 12% or higher.

9. The method of claim 1, wherein the solid fraction has a dry matter content of 40% or higher.

10. The method of claim 1, wherein monomer xylose yield after post-hydrolysis is at least 60% of theoretical maximal yield.

11. The method of claim 1, wherein monomer glucose yield after hydrolysis is at least 60% of theoretical maximal yield.

12. The method of claim 1, wherein the enzymatic hydrolysis is conducted using a commercially available cellulase preparation optimized for lignocellulosic biomass conversion.

13. The method of claim 1, wherein the enzymatic hydrolysis is conducted for at least 96 hours.

14. The method of claim 1, wherein the enzymatic hydrolysis is conducted at between 15% and 23% dry matter content or at 20% or higher dry matter content.

15. The method of claim 1, wherein the enzymatic hydrolysis is conducted using the enzyme mixture comprising exocellulase activities (EC 3.2.1.91), endocellulase activity (EC 3.2.1.4), beta-glucosidase activity (EC 3.2.1.21), beta-1,4 endoxylanase activity (EC 3.2.1.8), and acetyl xylan esterase activity (EC 3.1.1.72), and wherein the enzyme mixture is further characterized by having comprises relative proportions of the enzyme activities such that 1 filter paper units (FPU) of cellulase activity is associated with at least 30 carboxymethycellulose units (CMC U) of endoglucanase activity and with at least 28 para-nitrophenyl-beta-D-glucopyranoside units (pNPG U) of beta-glucosidase activity and with at least 50 birchwood xylanase units (ABX U) of endoxylanase activity.

16. The method of claim 15, wherein the enzyme mixture further comprises beta-1,3 xylosidase activity (EC 3.2.1.72), beta-1,4 xylosidase activity (EC 3.2.1.37), and alpha-1,3 and/or alpha-1,5 arabinofuranosidase activity (EC 3.2.1.23).

17. The method of claim 1, wherein a combined C5/C6 hydrolysate recovered after post-hydrolysis of the liquid fraction is directly fermented to ethanol using one or more modified yeast strains.

18. The method of claim 1, wherein the solid fraction comprises insoluble solids with greater than 50% of associated dissolved solids removed.

19. The method of claim 1, wherein at least 85% of the xylo-oligomers present in the liquid fraction are hydrolysed to the xylose monomers during post-hydrolysis.

20. The method of claim 1, wherein the liquid fraction is added to hydrolysed solid fraction after at least 50% cellulose conversion to glucose has been obtained.

* * * * *